United States Patent
Yokoyama et al.

(10) Patent No.: US 12,053,564 B2
(45) Date of Patent: Aug. 6, 2024

(54) BLOOD PURIFICATION DEVICE

(71) Applicant: NIKKISO CO., LTD., Tokyo (JP)

(72) Inventors: Takayoshi Yokoyama, Makinohara (JP); Masato Fujiwara, Makinohara (JP); Hiroshi Nimura, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 540 days.

(21) Appl. No.: 17/269,819

(22) PCT Filed: Aug. 27, 2019

(86) PCT No.: PCT/JP2019/033423
§ 371 (c)(1),
(2) Date: Feb. 19, 2021

(87) PCT Pub. No.: WO2020/045384
PCT Pub. Date: Mar. 5, 2020

(65) Prior Publication Data
US 2021/0316055 A1    Oct. 14, 2021

(30) Foreign Application Priority Data
Aug. 27, 2018 (JP) .................. 2018-158106

(51) Int. Cl.
*A61M 1/16* (2006.01)
*A61M 1/14* (2006.01)
(Continued)

(52) U.S. Cl.
CPC ...... *A61M 1/1696* (2013.01); *A61M 1/15632* (2022.05); *A61M 1/3621* (2013.01);
(Continued)

(58) Field of Classification Search
CPC .............. A61M 1/3644; A61M 1/3643; A61M 1/3647; A61M 1/1696; A61M 1/15632;
(Continued)

(56) References Cited

U.S. PATENT DOCUMENTS 4,713,171 A * 12/1987 Polaschegg ......... A61M 1/3646
422/44
4,976,593 A * 12/1990 Miyamoto .......... A61M 60/538
417/475
(Continued)

FOREIGN PATENT DOCUMENTS

CN  106237413 A  12/2016
EP  1518572 A1  3/2005
(Continued)

OTHER PUBLICATIONS

Apr. 4, 2023 Office Action issued in Japanese Patent Application No. 2020-539465.
(Continued)

*Primary Examiner* — Philip R Wiest
*Assistant Examiner* — Matthew Wrubleski
(74) *Attorney, Agent, or Firm* — Oliff PLC

(57) ABSTRACT

A lid that retains a pump tube which is elastic; a finger driving unit that is disposed facing the lid with the pump tube interposed therebetween, and that causes a plurality of fingers to sequentially move in the direction of contacting and separating from the lid; and a pump tube opening/closing mechanism that causes the finger driving unit to advance towards and retract from the lid, and that closes and opens the pump tube which is disposed between the fingers and the lid.

12 Claims, 34 Drawing Sheets

(51) Int. Cl.
  *A61M 1/36* (2006.01)
  *A61M 60/113* (2021.01)
  *A61M 60/279* (2021.01)
  *A61M 60/37* (2021.01)
  *A61M 60/847* (2021.01)

(52) U.S. Cl.
  CPC .. *A61M 1/362227* (2022.05); *A61M 1/36225* (2022.05); *A61M 60/113* (2021.01); *A61M 60/279* (2021.01); *A61M 60/37* (2021.01); *A61M 60/847* (2021.01); *A61M 1/155* (2022.05); *A61M 1/1562* (2022.05); *A61M 2205/126* (2013.01); *A61M 2205/702* (2013.01)

(58) Field of Classification Search
  CPC .. A61M 1/155; A61M 1/1562; A61M 60/279; A61M 60/113; A61M 60/37; A61M 60/847; A61M 60/441; A61M 2205/126; A61M 2205/702; A61M 2205/12; A61M 2205/123
  See application file for complete search history.

(56) References Cited

U.S. PATENT DOCUMENTS

| | | | |
|---|---|---|---|
| 5,062,775 A | | 11/1991 | Orth |
| 5,211,548 A | * | 5/1993 | Okada ............... A61M 5/14228 417/474 |
| 5,429,485 A | * | 7/1995 | Dodge ................. A61M 5/142 604/152 |
| 8,834,399 B2 | | 9/2014 | Muller-Spanka et al. |
| 2005/0069436 A1 | | 3/2005 | Shibasaki |
| 2013/0177455 A1 | | 7/2013 | Kamen et al. |
| 2018/0071445 A1 | | 3/2018 | Suzuki |

FOREIGN PATENT DOCUMENTS

| | | | |
|---|---|---|---|
| JP | 2000-107281 A | | 4/2000 |
| JP | 2007-296134 A | | 11/2007 |
| JP | 2008-178444 A | | 8/2008 |
| JP | 2013-248337 A | | 12/2013 |
| JP | 2015-021458 A | | 2/2015 |
| JP | 5934581 B2 | * | 6/2016 |
| JP | 5934581 B2 | | 6/2016 |
| JP | 2016-125413 A | | 7/2016 |
| JP | 2016-187591 A | | 11/2016 |
| JP | 2016-220958 A | | 12/2016 |
| JP | 2016220958 A | * | 12/2016 |
| WO | 2010/093946 A1 | | 8/2010 |

OTHER PUBLICATIONS

May 9, 2022 Search Report issued in European Patent Application No. 19855616.9.
Nov. 12, 2019 Search Report issued in International Patent Application No. PCT/JP2019/033423.
Apr. 27, 2020 International Preliminary Report on Patentability issued in International Patent Application No. PCT/JP2019/033423.
Sep. 26, 2023 Office Action issued in Chinese Patent Application No. 201980055408.X.

* cited by examiner

DETAILS OF PORTION C

DETAILS OF PORTION E
CROSS SECTION F-F

BLOOD PURIFICATION DEVICE

CROSS-REFERENCE TO RELATED APPLICATION

This application is a National Stage of PCT international application Ser. No. PCT/JP2019/033423 filed on Aug. 27, 2019 which designates the United States, and also claims priority to Japanese Patent Application No. 2018-158106 filed on Aug. 27, 2018, incorporated herein by reference.

TECHNICAL FIELD

The present invention relates to a structure of a blood purification device.

BACKGROUND

In a blood purification device having a roller pump in which a pump tube constituting a part of a liquid circuit is held by a tube receiver and in which the pump tube is pressed with a roller so that a liquid inside the pump tube is delivered, a method of occluding and releasing the pump tube by pressing the tube receiver against the roller is being used (for example, see Patent Document 1).

Further, in a blood purification device, a plurality of roller pumps are often used. For such cases, it has been suggested to drive and control the individual roller pumps with separate control devices (for example, see Patent Document 2).

CITATION LIST

Patent Literature

Patent Document 1: JP 5934581 B
Patent Document 2: JP 2000-107281 A

SUMMARY

Technical Problem

In a blood purification device, in addition to operations of priming the liquid circuit and performing hemodialysis, an operation such as calibration of the pump discharge flow rate may be performed. In that case, it is necessary to configure a liquid circuit for the special operation by blocking a part of the liquid circuit or allowing a part of the liquid circuit to be bypassed. Conventionally, a liquid circuit required for an operation is often configured by manually opening and closing a liquid circuit using a valve.

Meanwhile, in a blood purification device, several pumps are often used as described in Patent Document 2, and accordingly, the number of times of the opening and closing of the liquid circuit is increased. It is therefore desired that a liquid circuit necessary for an operation be configured not manually but automatically by the blood purification device.

As a method to that end, there might be considered, for example, a method of opening and closing a pump tube by pressing a tube receiver of a roller pump against a roller as described in Patent Document 1. However, when the number of pumps and the number of liquid circuits are increased, a pump tube opening/closing control mechanism must be provided for every pump, and this results in the problem that the device configuration becomes complicated.

In view of the above, the present invention is directed to carrying out opening and closing of a liquid circuit in a blood purification device by means of a simple configuration.

Solution to Problem

A blood purification device according to the present invention comprises: a tube receiving plate that holds an elastic pump tube; a tube pressing member driving unit which is positioned facing the tube receiving plate across the pump tube, and which causes a tube pressing member to be moved with respect to the tube receiving plate; and a pump tube opening/closing mechanism that causes the tube pressing member driving unit and the tube receiving plate to advance and retract relative to each other, and thereby carries out closing and opening of the pump tube which is positioned between the tube pressing member and the tube receiving plate.

In this way, since the pump tube is opened and closed by causing the tube pressing member driving unit to advance and retract relative to the tube receiving plate by means of the pump tube opening/closing mechanism, the opening and closing of the liquid circuit can be carried out with a simple configuration.

In the blood purification device of the present invention, the pump tube opening/closing mechanism may comprise a cam that causes the tube pressing member driving unit to advance toward the tube receiving plate, and a retraction mechanism that causes the tube pressing member driving unit to retract from the tube receiving plate.

With this arrangement, opening and closing of a liquid circuit can be carried out with a simple configuration comprising the cam and the retraction mechanism.

In the blood purification device of the present invention, the tube receiving plate may hold a plurality of pump tubes, and a plurality of tube pressing member driving units may be provided. The pump tube opening/closing mechanism may comprise: a plurality of cams that cause the plurality of tube pressing member driving units to advance toward the tube receiving plate; a common cam driving unit that rotates and drives the plurality of cams; and a plurality of retraction mechanisms that cause the plurality of tube pressing member driving units to retract from the tube receiving plate. The pump tube opening/closing mechanism may cause the cam driving unit to drive the plurality of cams so that the plurality of tube pressing member driving units are caused to advance and retract with respect to the tube receiving plate, and thereby carry out closing and opening of the plurality of pump tubes, which are positioned between the plurality of tube pressing members of the plurality of tube pressing member driving units and the tube receiving plate.

Since the closing and opening of the plurality of pump tubes can be performed by causing the common cam driving unit to drive the plurality of cams, opening and closing of a large number of liquid circuits can be carried out with a simple configuration.

In the blood purification device of the present invention, the plurality of cams may have shapes corresponding to combinations of open and closed states of the plurality of pump tubes.

According to this arrangement, various liquid circuits can be configured by combining various types of cams, and the blood purification device can be operated in various operation patterns.

The blood purification device of the present invention may comprise a device main body inside of which the tube pressing member driving unit and the pump tube opening/closing mechanism are arranged, and the tube receiving plate may be a plate located facing the device main body. Further, the blood purification device may comprise a cassette that is detachably mounted to the device main body, wherein the cassette includes a casing, which contains a dialyzer, a dialysate regeneration column, and a water removal container, and wherein the tube receiving plate is a plate of the casing that is located facing the device main body.

In the blood purification device comprising the cassette integrating a liquid-contacting section and the device main body, the opening and closing of the pump tube are carried out by arranging the tube pressing member driving unit and the pump tube opening/closing mechanism, which are non-liquid-contacting sections, in the non-disposable device main body, while the cassette integrating the liquid-contacting section is configured disposable. With this arrangement, handling of the blood purification device can be simplified, and the opening and closing of the liquid circuit can be performed with a simple configuration.

In the blood purification device of the present invention, the pump tube opening/closing mechanism may include a cam that causes the tube receiving plate to advance toward the tube pressing member driving unit, and a retraction mechanism that causes the tube receiving plate to retract from the tube pressing member driving unit. Further, in the blood purification device of the present invention, the tube receiving plate may hold a plurality of pump tubes, and a plurality of tube pressing member driving units may be provided. The cam of the pump tube opening/closing mechanism may cause the tube receiving plate to advance toward the plurality of tube pressing member driving units, and thereby carry out closing and opening of the plurality of pump tubes, which are positioned between the plurality of tube pressing members of the plurality of tube pressing member driving units and the tube receiving plate.

In the blood purification device of the present invention, the retraction mechanism may be a retraction spring, and the tube pressing member may be composed of a plurality of fingers.

In the blood purification device of the present invention, the pump tube opening/closing mechanism may include a cam that causes the tube pressing member driving unit to advance toward the tube receiving plate via a cam follower which is attached to the tube pressing member driving unit via an elastic member, and a retraction mechanism that causes the tube pressing member driving unit to retract from the tube receiving plate.

By adopting a configuration as described above in which the cam follower is attached to the tube pressing member driving unit via the elastic member, and in which the tube pressing member driving unit is caused to advance toward the tube receiving plate via this cam follower, the closing and opening of the pump tube can be performed reliably even without accurate adjustment of the advancing distance of the tube pressing member driving unit.

According to the present invention, the tube receiving plate may hold a plurality of pump tubes, and a plurality of tube pressing member driving units may be provided. The pump tube opening/closing mechanism may comprise: a plurality of cams which abut cam followers respectively attached to the plurality of tube pressing member driving units via elastic members and which cause the plurality of tube pressing member driving units to advance toward the tube receiving plate; a common cam driving unit that rotates and drives the plurality of cams; and a plurality of retraction mechanisms that cause the plurality of tube pressing member driving units to retract from the tube receiving plate. The pump tube opening/closing mechanism may cause the cam driving unit to drive the plurality of cams so that the plurality of tube pressing member driving units are caused to advance and retract with respect to the tube receiving plate, and thereby carries out closing and opening of the plurality of pump tubes, which are positioned between the plurality of tube pressing members of the plurality of tube pressing member driving units and the tube receiving plate. The plurality of cams may have shapes corresponding to combinations of open and closed states of the plurality of pump tubes. Further, in the blood purification device of the present invention, when the pump tube opening/closing mechanism closes the pump tube, a front end of the tube pressing member driving unit may abut a surface of the tube receiving plate.

Since the closing and opening of the plurality of pump tubes can be performed by driving the plurality of cams with the common cam driving unit, closing and opening of a large number of liquid circuits can be carried out with a simple configuration. Further, various liquid circuits can be configured by combining various types of cams, and the blood purification device can be operated in various operation patterns.

The blood purification device of the present invention may comprise a device main body inside of which the tube pressing member driving unit and the pump tube opening/closing mechanism are arranged, and a cover attached facing the device main body. The tube receiving plate may be attached to the cover via another elastic member.

According to the present configuration, the closing and opening of the pump tubes can be performed reliably even without accurate adjustment of the advancing distance of the tube pressing member driving units.

In the blood purification device of the present invention, a plurality of tube pressing member driving units may be provided. The cover may have a plurality of recesses at positions facing the tube pressing members of the tube pressing member driving units. In each of the recesses, a tube receiving plate may be mounted via an elastic member, and each of the tube receiving plates may hold a corresponding pump tube. The pump tube opening/closing mechanism may comprise: a plurality of cams that cause the plurality of tube pressing member driving units to advance toward the tube receiving plates; a common cam driving unit that rotates and drives the plurality of cams; and a plurality of retraction mechanisms that cause the plurality of tube pressing member driving units to retract from the tube receiving plates. The pump tube opening/closing mechanism may cause the cam driving unit to drive the plurality of cams so that the plurality of tube pressing member driving units are caused to advance and retract with respect to the tube receiving plates, and thereby carry out closing and opening of the plurality of pump tubes, which are positioned between the plurality of tube pressing members of the plurality of tube pressing member driving units and the tube receiving plates. The plurality of cams may have shapes corresponding to combinations of open and closed states of the plurality of pump tubes. Further, in the blood purification device of the present invention, the elastic members and said other elastic member may be composed of springs.

Since the closing and opening of the plurality of pump tubes can be performed by driving the plurality of cams with the common cam driving unit, closing and opening of a large number of liquid circuits can be carried out with a simple configuration. Further, various liquid circuits can be configured by combining various types of cams, and the blood purification device can be operated in various operation patterns.

Accordingly, with a simple configuration, the closing and opening of the pump tubes can be performed reliably even without accurate adjustment of the advancing distance of the tube pressing member driving units.

The blood purification device of the present invention may include a cam follower attached to the tube pressing member driving unit via an elastic member, and the cam may cause the tube receiving plate to advance toward the tube pressing member driving unit via the cam follower. The tube receiving plate and the tube pressing member driving unit may be connected via another elastic member. Further, the elastic member and said other elastic member may be composed of springs.

According to this configuration, the closing and opening of the pump tube can be performed reliably even without accurate adjustment of the advancing distance of the tube pressing member driving unit.

Advantageous Effects of Invention

The present invention enables to carry out opening and closing of a liquid circuit in a blood purification device by means of a simple configuration.

DESCRIPTION OF EMBODIMENTS

A blood purification device 100 according to an embodiment is described below by reference to the drawings. The blood purification device 100 comprises a device main body 10, and a cover 30 attached to the device main body 10 in a manner capable of being opened and closed. In the following description, the direction in which the device main body 10 and the cover are arranged will be referred to as the front-rear direction, the direction orthogonal to the front-rear direction in a horizontal plane will be referred to as the width direction, and the upright direction will be referred to as the vertical direction.

Figure 1:
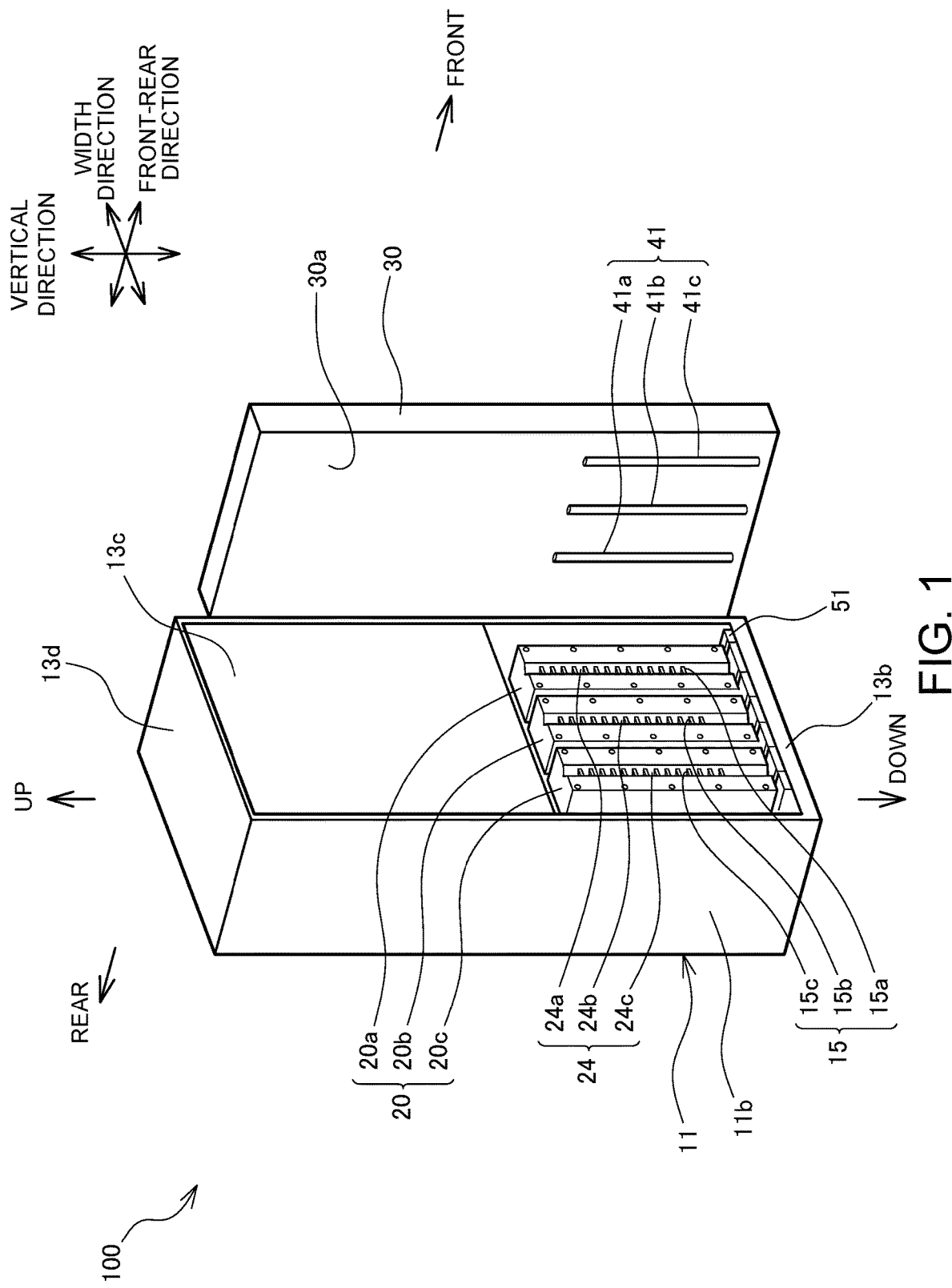
FIG. 1 is a perspective view of a blood purification device according to an embodiment.
Figure 2:
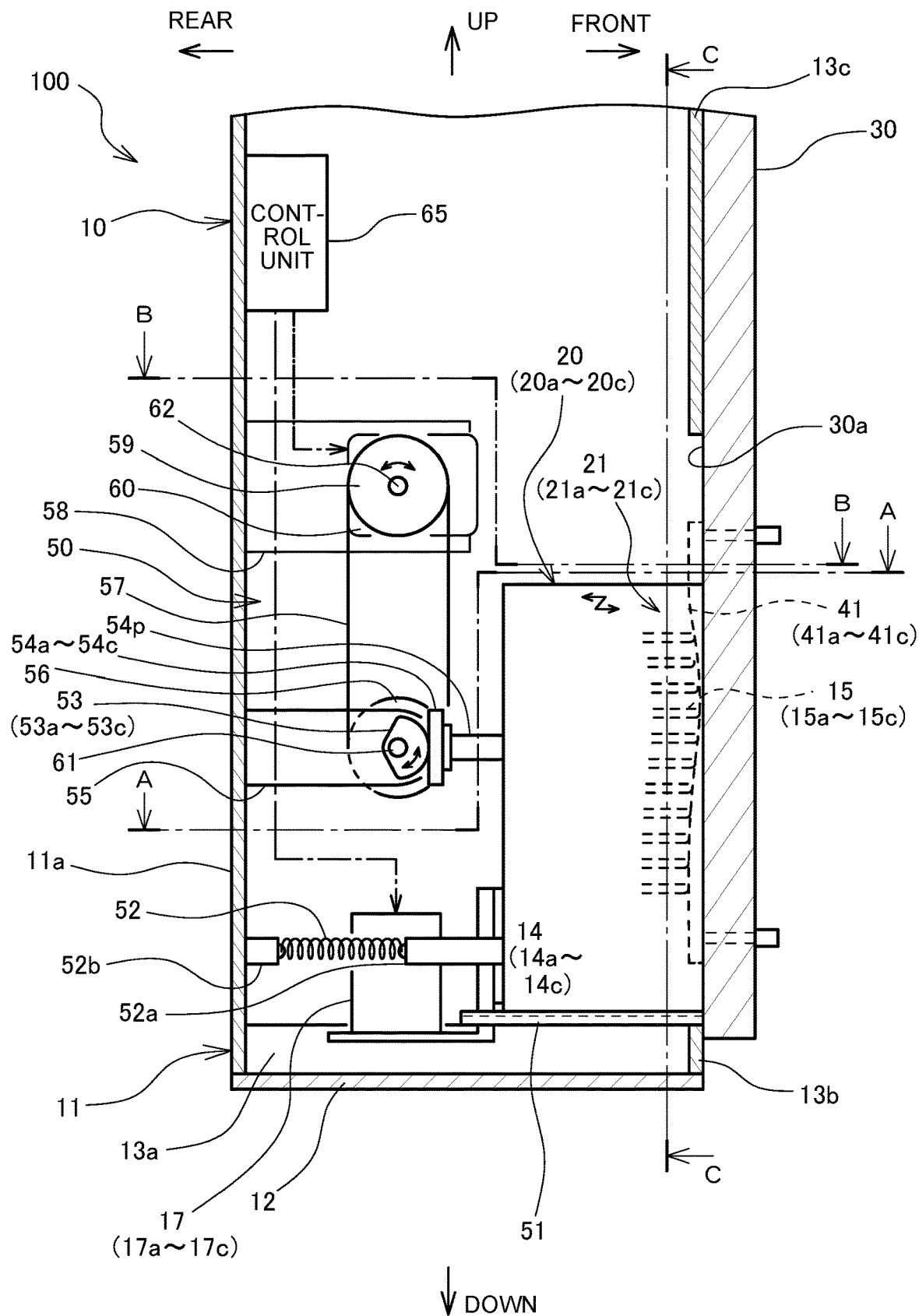
FIG. 2 is an elevational sectional view of the blood purification device according to the embodiment.

As shown in FIGS. 1 and 2, the device main body 10 includes a housing 11, finger driving units 20 which are a plurality of tube pressing member driving units received inside the housing 11, a common pump tube opening/closing mechanism 50, and a common control unit 65.

Configuration of Finger Driving Units

Figure 3:
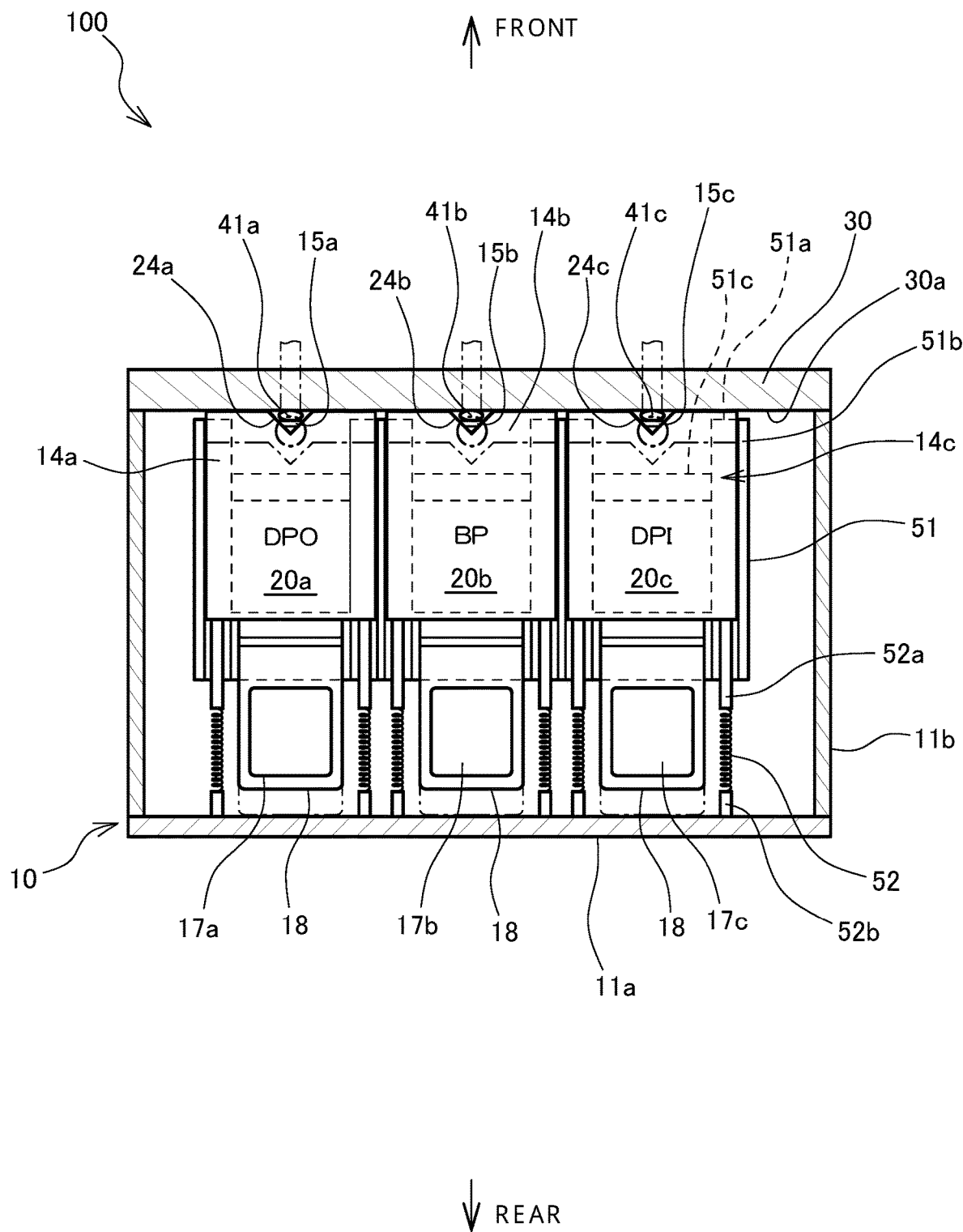
FIG. 3. is a plan sectional view showing a cross-section A-A of FIG. 2.

As shown in FIGS. 2 and 3, each of the finger driving units 20 (20a-20c) comprises a finger casing 14 (14a-14c) and a drive motor 17 (17a-17c). Each finger casing 14 (14a-14c) has a finger support portion 21 (21a-21c). The finger support portion 21 (21a-21c) supports fingers 15 (15a-15c), which are tube pressing members arranged in a plurality of rows in the vertical direction, in a front part of the finger casing 14 (14a-14c) in such a manner that the fingers 15 are movable in the front-rear direction of the device main body 10 while being housed inside the housing 11 of the device main body 10. In the front surface of each finger casing 14 (14a-14c), a V-shaped tube receiving groove 24 (24a-24c) is formed extending vertically. Here, the tube receiving grooves 24 may alternatively be not provided. Instead of the V-shaped grooves, plate-shaped guides extending in the vertical direction may be provided so as to prevent twisting of pump tubes 41a-41c (described further below).

The respective drive motors 17 (17a-17c) drive the fingers 15 (15a-15c), which are the tube pressing members, in the front-rear direction of the device main body 10. The drive motors 17 are connected to the control unit 65 and are operated according to commands from the control unit 65.

Configuration of Housing

Figure 5:
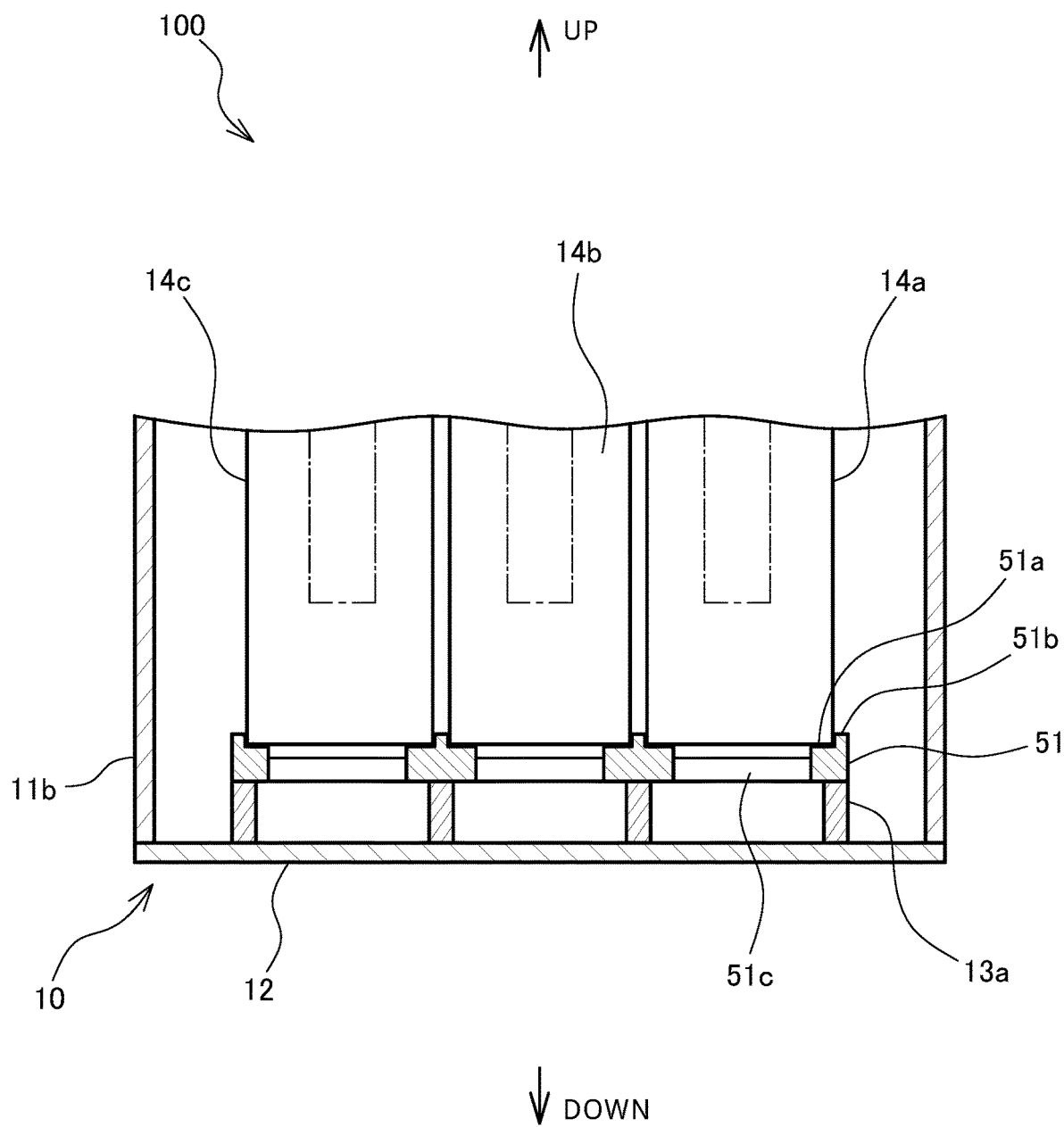
FIG. 5 is an elevational sectional view showing a cross-section C-C of FIG. 2.

As shown in FIGS. 1 and 2, the housing 11 includes: a base 12; a rear plate 11a provided upright toward the rear end of the base 12; side plates 11b provided upright on both sides in the width direction of the base 12; a width plate 13b provided upright toward the front end of the base 12; a front plate 13c covering an upper part of the front side of the device main body 10; and a ceiling plate 13d. As shown in FIG. 5, a plurality of ribs 13a extending in the front-rear direction are provided on the upper surface of the base 12.

Configuration of Pump Tube Opening/Closing Mechanism

As shown in FIGS. 2 to 5, the pump tube opening/closing mechanism 50 includes: a casing guide 51 that supports the finger casings 14 (14a-14c) in a manner slidable in the front-rear direction; rotary cams 53 (53a-53c) that cause the finger driving units 20 (20a-20c) to advance toward the cover 30; coil springs 52 which are retraction springs constituting a retraction mechanism that causes the finger driving units 20 (20a-20c) to retract from the cover 30; and a motor 60 that rotates and drives the rotary cams 53 (53a-53c).

The casing guide 51 includes a plurality of support plates 51a, guide bars 51b, and connecting members 51c. As shown in FIGS. 3 and 5, the support plates 51a are plate members extending in a longitudinal direction, which are attached to the upper ends of the plurality of ribs 13a provided on the upper surface of the base 12, and which support the bottom surfaces of the lower corners of the finger casings 14 (14a-14c). The guide bars 51b are plate members provided upright on the upper surfaces of the support plates 51a and extending in the longitudinal direction, which guide the side surfaces of the lower corners of the finger casings 14 (14a-14c) in the front-rear direction. The connecting members 51c are plate members that connect between the support plates 51a in the width direction. As shown in FIG. 5, each of the support plates 51a located at the two widthwise ends supports the bottom surface of a lower corner of one finger casing 14 (14a or 14c), and each of the guide bars 51b provided upright on the upper surfaces of these support plates 51a located at the two widthwise ends guides a side surface of one finger casing 14 (14a or 14c) in the front-rear direction. Further, each of the two central support plates 51a supports the bottom surfaces of lower corners of two adjacent finger casings 14 (14a-14c), and each of the guide bars 51b provided upright on the upper surfaces of these two central support plates 51a guides side surfaces of two adjacent finger casings 14 (14a-14c) in the front-rear direction. Here, the casing guide 51 may be any member that guides the finger casings 14 (14a-14c) in the front-rear direction, and is not limited to the above-described configuration.

As shown in FIGS. 2 and 3, at both widthwise side portions of a lower part of the rear surface of each finger casing 14 (14a-14c), pins 52a are attached, to each of which one end of the respective coil spring 52 is to be mounted. Further, pins 52b are attached to the rear plate 11a of the device main body 10 at positions facing the respective pins 52a. The coil springs 52 are mounted between the pins 52a and the pins 52b. Here, the finger casings 14 (14a-14c) and the rear plate 11a may alternatively be connected directly by the coil springs 52 without using the pins 52a and 52b.

Figure 4:
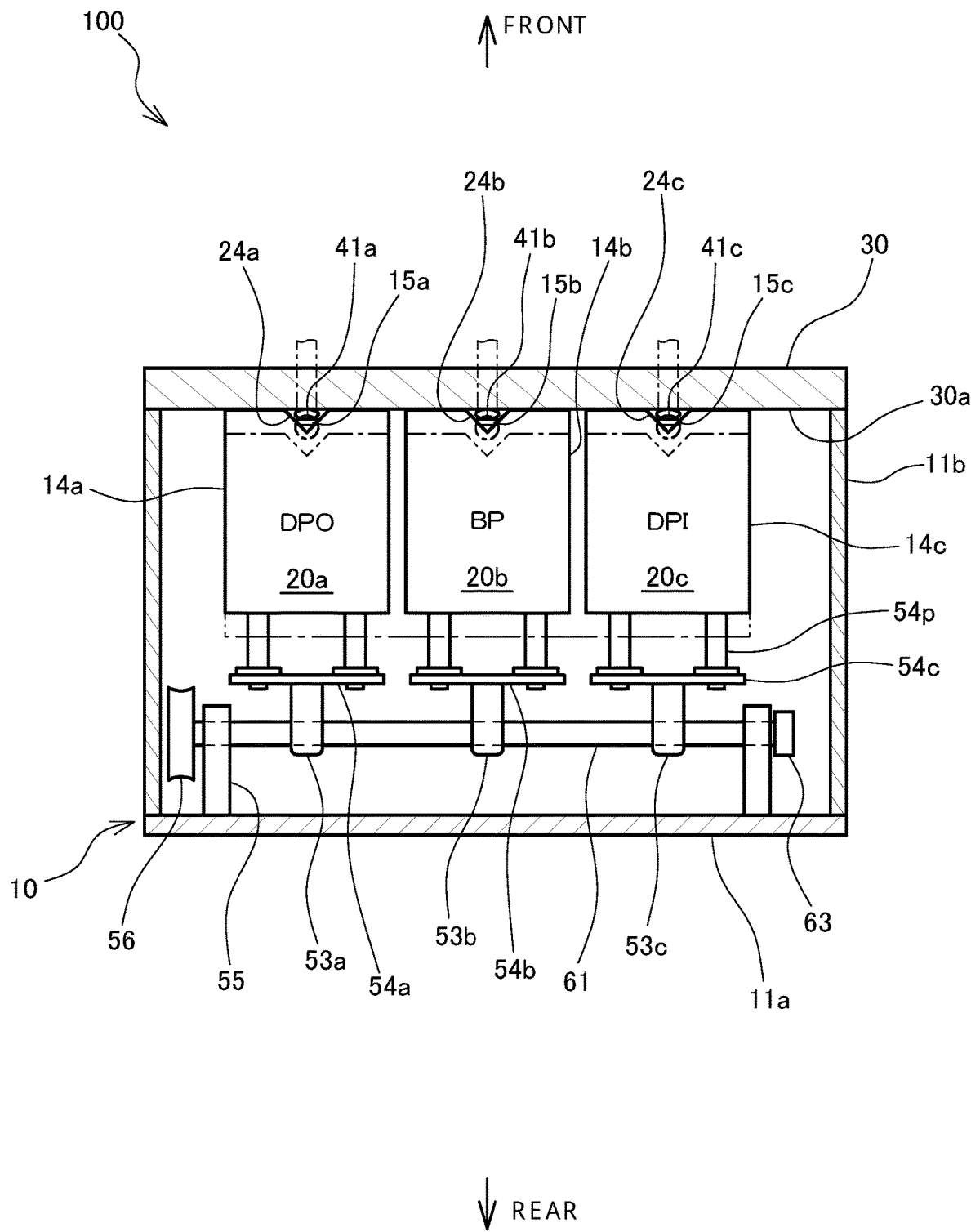
FIG. 4 is a plan sectional view showing a cross-section B-B of FIG. 2.

As shown in FIGS. 2 and 4, at both widthwise side portions of the rear plate 11a of the device main body 10, brackets 55 are attached, which rotatably support a shaft 61 to which the rotary cams 53 (53a-53c) are mounted. A pulley 56 is attached to one end of the shaft 61, while a collar 63 is attached to the other end. At a portion of the rear plate 11a above the brackets 55, a bracket 58 is attached, and the motor 60 is fixed to the bracket 58. A pulley 59 is attached to a shaft 62 of the motor 60. The pulley 59 attached to the shaft 62 of the motor 60 and the pulley 56 attached to the shaft 61 to which the rotary cams 53 (53a-53c) are mounted are connected by a belt 57. The motor 60 is connected to the control unit 65 and is operated according to commands from the control unit 65. The motor 60, the pulleys 59 and 56, the belt 57, and the shaft 61 constitute a common cam driving unit that drives the plurality of rotary cams 53 (53a-53c).

As shown in FIGS. 2 and 4, at both widthwise side portions of a central part, in the vertical direction, of the rear surface of each finger casing 14 (14a-14c), two posts 54p are attached. Between the pairs of posts 54p, plate-shaped cam followers 54a-54c are mounted, which are abutted by the rotary cams 53 (53a-53c). Here, alternatively, the posts 54p and the cam followers 54a-54c may be not provided, and the rotary cams 53 may be configured to contact the rear surfaces of the finger casings 14 (14a-14c).

Configuration of Cover

As shown in FIGS. 1 and 2, the cover 30 is a flat plate member, and has the pump tubes 41a-41c mounted on its flat surface 30a located toward the device main body 10 (i.e., located toward the rear). The two ends of the pump tubes 41a-41c are connected to a blood circuit 91 and a dialysate circuit 92 shown in FIG. 6(a). The surfaces of the pump tubes 41a-41c located toward the cover 30 are arranged along the flat surface 30a of the cover 30. As such, the cover 30 constitutes a tube receiving plate that holds the pump tubes 41 (41a-41c). In FIGS. 6(a), 7(a), 8(a) and 9(a), illustration of a dialysate regeneration column 38 provided in the dialysate circuit 92 is omitted. The dialysate regeneration column 38 may be provided at any position in the dialysate circuit 92.

When the cover 30 is closed, as shown in FIGS. 2 to 4, the pump tubes 41 (41a-41c) are received in the tube receiving grooves 24 (24a-24c) of the finger casings 14 (14a-14c), and the finger driving units 20 (20a-20c) are arranged facing the cover 30 across the pump tubes 41 (41a-41c). Here, the cover 30 need not be a flat plate member so long as the cover 30 has sufficient hardness for collapsing the pump tubes 41 (41a-41c) in cooperation with the fingers 15a-15c.

When the motor 60 of the pump tube opening/closing mechanism 50 is rotated, the rotary cams 53 (53a-53c) are rotated via the pulleys 59, 56 and the belt 57. When the rotary cams 53 (53a-53c) are rotated and come into contact with the cam followers 54a-54c attached to the finger casings 14 (14a-14c), the cam followers 54a-54c are pushed forward toward the cover 30. When the cam followers 54a-54c are pushed forward, the finger casings 14 (14a-14c) are moved toward the cover 30 while being guided by the guide bars 51b of the casing guide 51. When the finger casings 14 (14a-14c) are moved toward the cover 30, the fingers 15 (15a-15c) are moved toward the cover 30, to thereby sandwich the pump tubes 41 (41a-41c) between the fingers 15 (15a-15c) and the cover 30, and to press the pump tubes 41 (41a-41c) against the surface 30a of the cover 30, so that the pump tubes 41 (41a-41c) become closed. At that time, the coil springs 52 are stretched out in the front-rear direction.

While in this state, when the drive motors 17 (17a-17c) of the finger driving units 20 (20a-20c) are rotated, the fingers 15 (15a-15c) arranged in a plurality of rows in the vertical direction are sequentially moved in the direction of approaching and moving away from the cover 30, so that liquid inside the pump tubes 41 (41a-41c) is delivered.

Further, when the rotary cams 53 are moved away from the cam followers 54a-54c, the coil springs 52 pull the pins 52a back toward the rear plate 11a of the housing 11. As a result, the finger casings 14 (14a-14c) are moved toward the rear of the device main body 10 so as to move away from the cover 30, while being guided by the guide bars 51b of the casing guide 51. When the finger casings 14 (14a-14c) are moved rearward, the fingers 15 (15a-15c) are moved in the direction away from the cover 30, and the fingers 15 (15a-15c) are moved out of contact with the surface of the pump tubes 41 (41a-41c), so that the pump tubes 41 (41a-41c) become opened.

Configuration of Rotary Cams

FIG. 6(b) shows the rotary cams 53a-53c mounted to the shaft 61. In FIG. 6(b), dash-dotted lines indicate the counterclockwise rotation angles of the shaft 61 and the rotary cams 53a-53c. The state shown in FIG. 6(b) is the initial position of the shaft 61 and the rotary cams 53a-53c.

As shown in FIG. 6(b), in the 0° rotation angle position, the rotary cams 53a and 53b have a small radius, and the cam followers 54a and 54b are placed in the rear open position. In the 90° and 180° rotation angle positions, the rotary cams 53a and 53b have a large radius, and the cam followers 54a and 54b are placed in the front closed position as shown in FIG. 7(b). Further, in the 90° rotation angle position, the rotary cam 53c has a large radius, and the cam follower 54c is placed in the front closed position as shown in FIG. 7(b). When in the 0° and 180° rotation angle positions, the rotary cam 53c has a small radius, and the cam follower 54c is placed in the rear open position as shown in FIGS. 6(b), 8(b), and 9(b). As such, the rotary cams 53a-53c have shapes according to combinations of open and closed states of the pump tubes 41a-41c.

Operation of Blood Purification Device

When the blood purification device 100 is in a stopped state, the shaft 61 is in the initial position in which, as shown in FIG. 6(b), the 0° position is located facing the cam followers 54a-54c, and all of the cam followers 54a-54c are in the rear open position. In this state, the fingers 15a-15c of a dialysate outlet pump DPO, a blood pump BP, and a dialysate inlet pump DPI are located away from the respective pump tubes 41a-41c, as shown by dash-dotted lines in FIGS. 3 and 4.

As shown in FIG. 7(a), in a dialysis operation, the dialysate outlet pump DPO and the dialysate inlet pump DPI are to be driven to circulate dialysate to a dialyzer 36 and a water removal container 37 in the dialysate circuit 92. Further, the blood pump BP is to be driven to cause blood from a human body to be delivered from a blood circuit inlet 91a to the dialyzer 36 and a drip chamber 39 in the blood circuit 91, and to be returned to the human body via a blood circuit outlet 91b. As such, in the dialysis operation, liquid delivering operation is to be carried out by the three pumps; namely, the dialysate outlet pump DPO, the dialysate inlet pump DPI, and the blood pump BP.

To this end, when performing the dialysis operation, the control unit 65 drives the motor 60 of the pump tube opening/closing mechanism 50 so as to rotate the shaft 61 by 90° from the initial position, to the position shown in FIG. 7(b). As shown in FIG. 7(b), when the shaft 61 is rotated by 90° from the initial position, the rotary cams 53a-53c are also rotated by 90° from the initial position, and all of the rotary cams 53a-53c push the cam followers 54a-54c forward into the front closed position. The finger casings 14a-14c are thereby moved forward. As a result, at least one finger 15a among the plurality of fingers 15a arranged in a plurality of rows in the vertical direction presses the pump tube 41a against the surface 30a of the cover 30, and closes the pump tube 41a. Similarly, at least one finger 15b and at least one finger 15c among the plurality of fingers 15b and 15c press the pump tubes 41b and 41c against the surface 30a of the cover 30, and close the pump tubes 41b and 41c. As a result, the pump tubes 41a, 41b, and 41c are placed in the closed state, and the dialysate outlet pump DPO, the blood pump BP, and the dialysate inlet pump DPI are placed in a state capable of delivering liquid.

Subsequently, the control unit 65 causes the drive motors 17a-17c of the finger driving units 20a-20c to rotate at a predetermined rotation speed. As a result, the fingers 15a-15c are sequentially moved in the direction of approaching and moving away from the cover 30, and a predetermined amount of liquid is delivered from the dialysate outlet pump DPO, the blood pump BP, and the dialysate inlet pump DPI. As shown in FIG. 7(a), the dialysate outlet pump DPO and the dialysate inlet pump DPI cause the dialysate to circulate through the dialyzer 36 and the water removal container 37 in the dialysate circuit 92, while the blood pump BP causes the blood from the human body to be delivered from the blood circuit inlet 91a to the dialyzer 36 and the drip chamber 39 in the blood circuit 91 and to be returned to the human body via the blood circuit outlet 91b.

In the blood purification device 100, priming is performed before the dialysis operation by, for example, circulating a physiological saline solution in the dialysate circuit 92 and the blood circuit 91. In priming the dialysate circuit 92, as shown in FIG. 8(*a*), the pump tube 41*c* of the dialysate inlet pump DPI is to be opened, and the priming solution is to be circulated to the dialysate circuit 92 using the dialysate outlet pump DPO.

Figure 8:
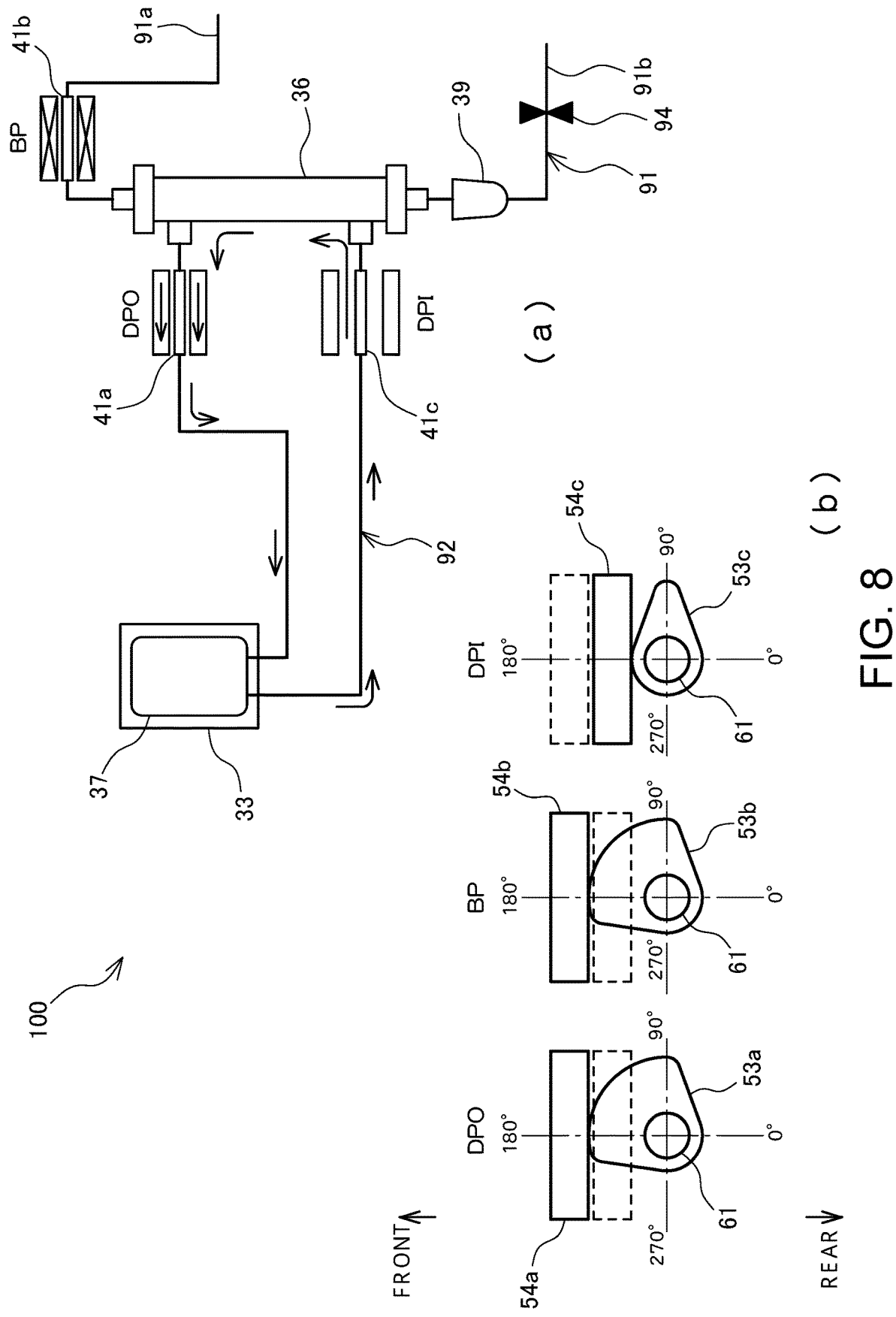
FIG. 8 is an explanatory diagram showing a liquid flow (a) and rotary cam positions (b) in the blood purification device during a priming operation.

To this end, when performing the priming, the control unit 65 drives the motor 60 of the pump tube opening/closing mechanism 50 so as to rotate the shaft 61 by 180° from the initial position to the position shown in FIG. 8(*b*). In the state shown in FIG. 8(*b*), the rotary cams 53*a* and 53*b* push the cam followers 54*a* and 54*b* forward to the closed position. On the other hand, the rotary cam 53*c* does not push the cam follower 54*c* forward, and the cam follower 54*c* that abuts the rotary cam 53*c* is in the rear open position. As a result, the finger casings 14*a* and 14*b* are moved forward, and the fingers 15*a* and 15*b* press the pump tubes 41*a* and 41*b* against the cover 30, so that the dialysate outlet pump DPO and the blood pump BP are placed in a state capable of delivering liquid. Meanwhile, the finger casing 14*c* is not moved forward, so that the fingers 15*c* are located away from the pump tube 41*c*, and the pump tube 41*c* of the dialysate inlet pump DPI is in the open state.

During the priming operation performed on the dialysate side, the blood circuit outlet 91*b* is closed by a valve 94 so that the priming solution is circulated in only the dialysate circuit 92. The control unit 65 rotates only the drive motor 17*a* of the finger driving unit 20*a* at a predetermined rotation speed. As a result, as in the above-described operation, a predetermined amount of liquid is delivered from the dialysate outlet pump DPO. As shown in FIG. 8(*a*), the dialysate outlet pump DPO causes the priming solution to be circulated through the dialyzer 36, the water removal container 37, and the pump tube 41*c* of the dialysate circuit 92.

Figure 9:
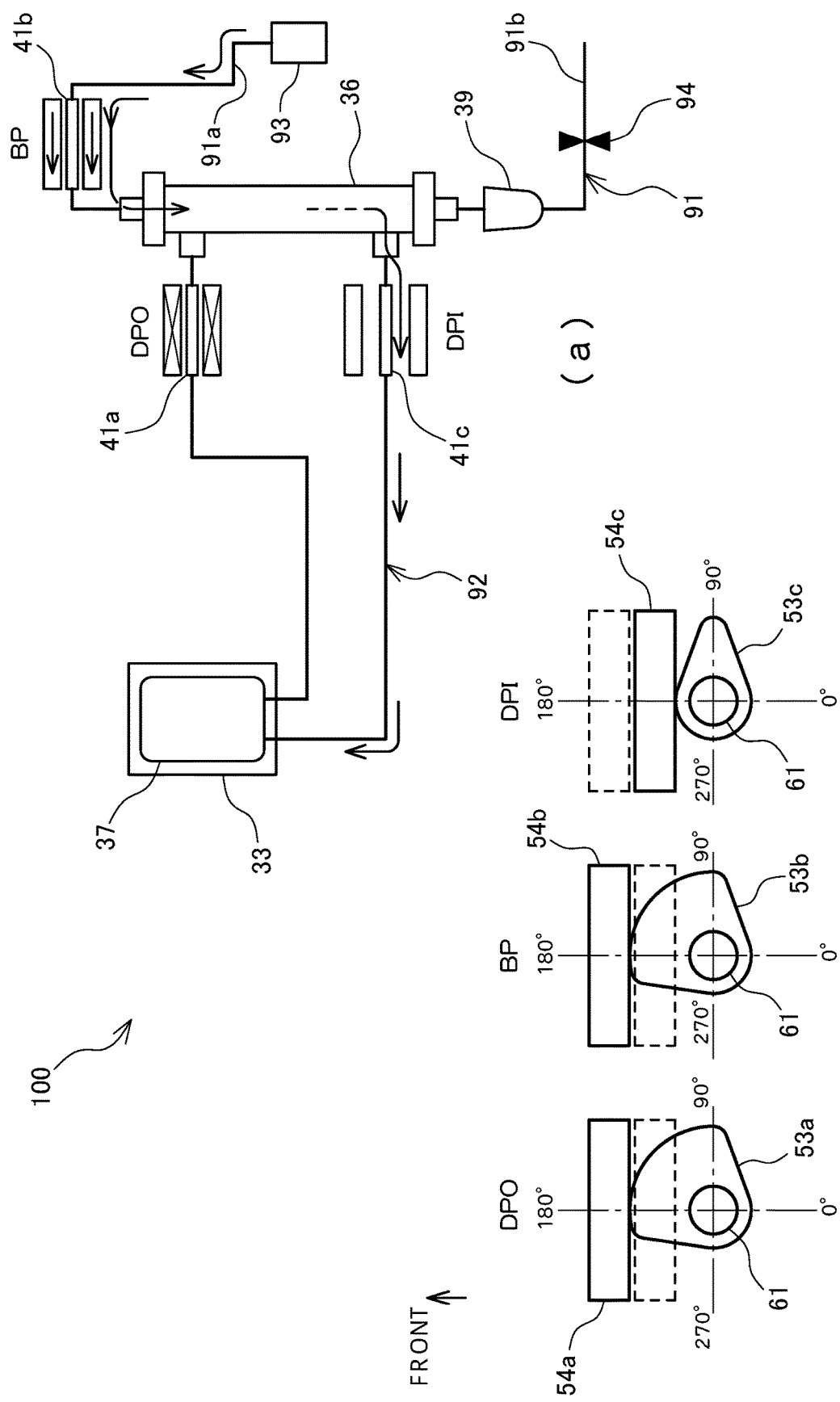
FIG. 9 is an explanatory diagram showing a liquid flow (a) and rotary cam positions (b) during a blood pump calibration operation.
Figure 10:
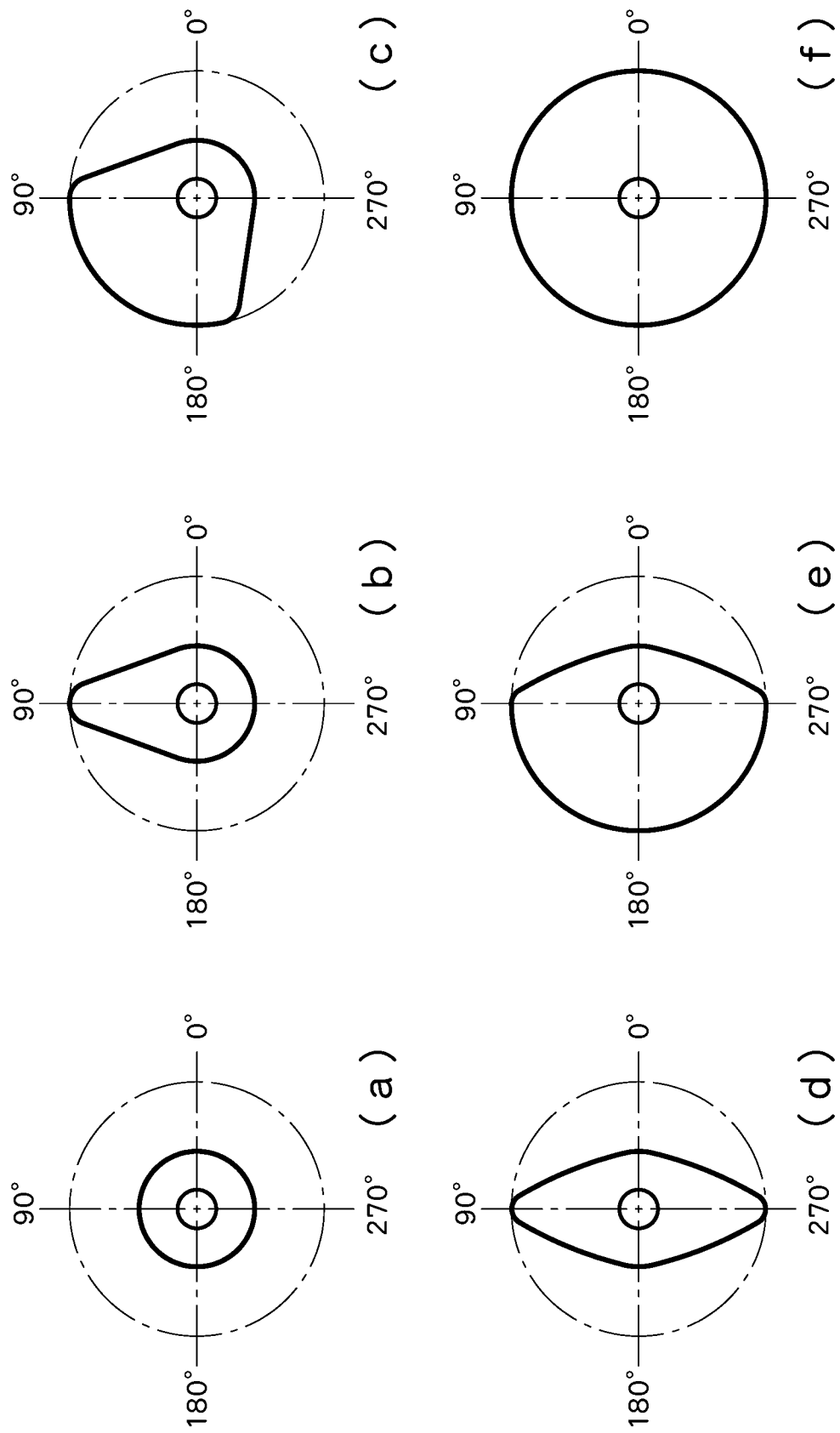
FIG. 10 is an explanatory diagram showing types of the rotary cams.

In the blood purification device 100, calibration of the liquid delivery amount of the blood pump BP may be performed. In that case, for example, a calibration liquid bag 93 containing a physiological saline solution or the like is connected to the blood circuit inlet 91*a* of the blood circuit 91, and the blood circuit outlet 91*b* is closed by the valve 94, as shown in FIG. 9(*a*). The pump tube 41*a* of the dialysate outlet pump DPO is to be closed while the pump tube 41*c* of the dialysate inlet pump DPI is opened, and the blood pump BP is to be driven so that the calibration liquid flows from the calibration liquid bag 93 through the dialyzer 36 and from the pump tube 41*c* of the dialysate inlet pump DPI to the water removal container 37. The weight of the water removal container 37 is detected by a weight detection unit 33 of the water removal container 37 so as to measure the liquid delivery amount of the blood pump BP. Based on this measurement, the liquid flow rate of the blood pump BP is to be calibrated.

To this end, when calibrating the liquid delivery amount of the blood pump BP, the control unit 65 drives the motor 60 of the pump tube opening/closing mechanism 50 so as to rotate the shaft 61 by 180° from the initial position to the position shown in FIG. 9(*b*). As a result, as in the operation described above by reference to FIG. 8(*b*), the dialysate outlet pump DPO and the blood pump BP are placed in a state capable of delivering liquid, and the pump tube 41*c* of the dialysate inlet pump DPI is opened.

Subsequently, the control unit 65 rotates the drive motor 17*b* of the finger driving unit 20*b* at a predetermined rotation speed, and a predetermined amount of liquid is thereby delivered from the blood pump BP, similar to the case of the above-described operation. Since the drive motor 17*a* is in the stopped state, the fingers 15*a* of the dialysate outlet pump DPO are in a state of closing the pump tube 41*a*. As shown in FIG. 9(*a*), the blood pump BP delivers the calibration liquid from the calibration liquid bag 93 through the dialyzer 36, and from the pump tube 41*c* of the dialysate inlet pump DPI to the water removal container 37. Based on a drive command value transmitted to the blood pump BP and a delivered liquid weight detected by the weight detection unit 33 of the water removal container 37, calibration of the blood pump BP is carried out.

As described above, in the blood purification device 100 of the present embodiment, the rotary cams 53*a*-53*c* have shapes corresponding to the combinations of open and closed states of the pump tubes 41*a*-41*c* necessary for the various operations of the blood purification device 100. Accordingly, by driving the single motor 60 of the pump tube opening/closing mechanism 50, the three finger casings 14 (14*a*-14*c*) can be caused to advance and retract with respect to the cover 30 so as to close and open the pump tubes 41 (41*a*-41*c*), and the dialysate circuit 92 and the blood circuit 91 can thereby be opened and closed in various patterns. In this way, in the blood purification device 100 including a plurality of pumps such as the dialysate outlet pump DPO, the dialysate inlet pump DPI, and the blood pump BP, various operations can be performed by a simple method.

In the blood purification device, there are cases in which the pump tubes 41*a*-41*c* are reused. Here, the term "reuse" means that consumables are not discarded after one blood purification treatment is completed, but are washed and disinfected as necessary and then used again for the next treatment. When the pump tubes 41*a*-41*c* are reused, the liquid delivery amount may become changed due to degradation caused by use.

In the blood purification device 100 of the present embodiment, as described by reference to FIGS. 9(*a*) and 9(*b*), calibration of the blood pump BP can be performed by driving the motor 60 of the pump tube opening/closing mechanism 50 to thereby close the pump tubes 41*a* and 41*b* and to place the pump tube 41*c* in the open state, and delivering a predetermined amount of liquid from the blood pump BP. Accordingly, even when the pump tube 41*b* is degraded by reuse, the blood pump BP can be easily calibrated to correct the flow rate.

Figure 6:
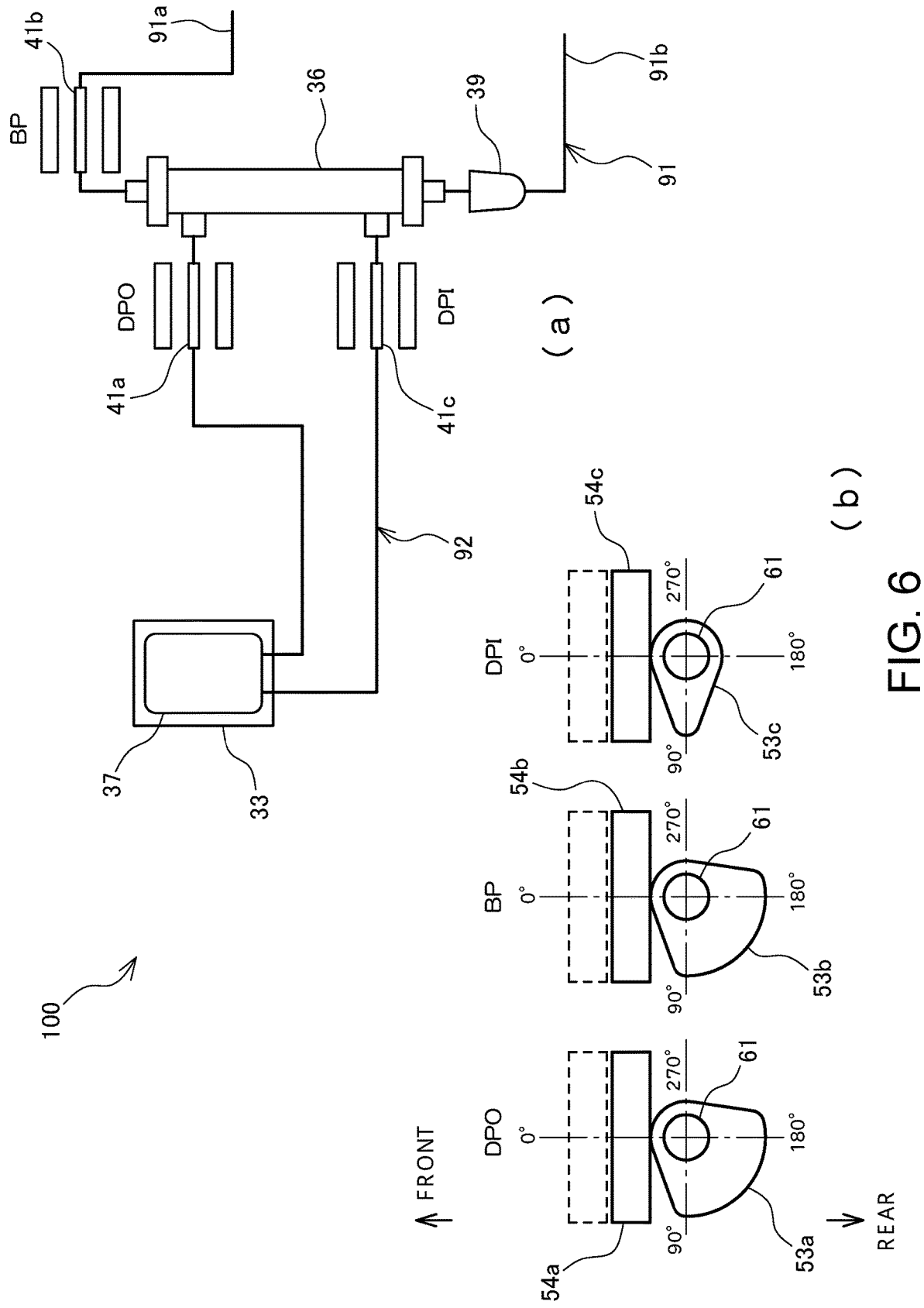
FIG. 6 is an explanatory diagram showing a configuration (a) and rotary cam positions (b) in the blood purification device in a stopped state.
Figure 7:
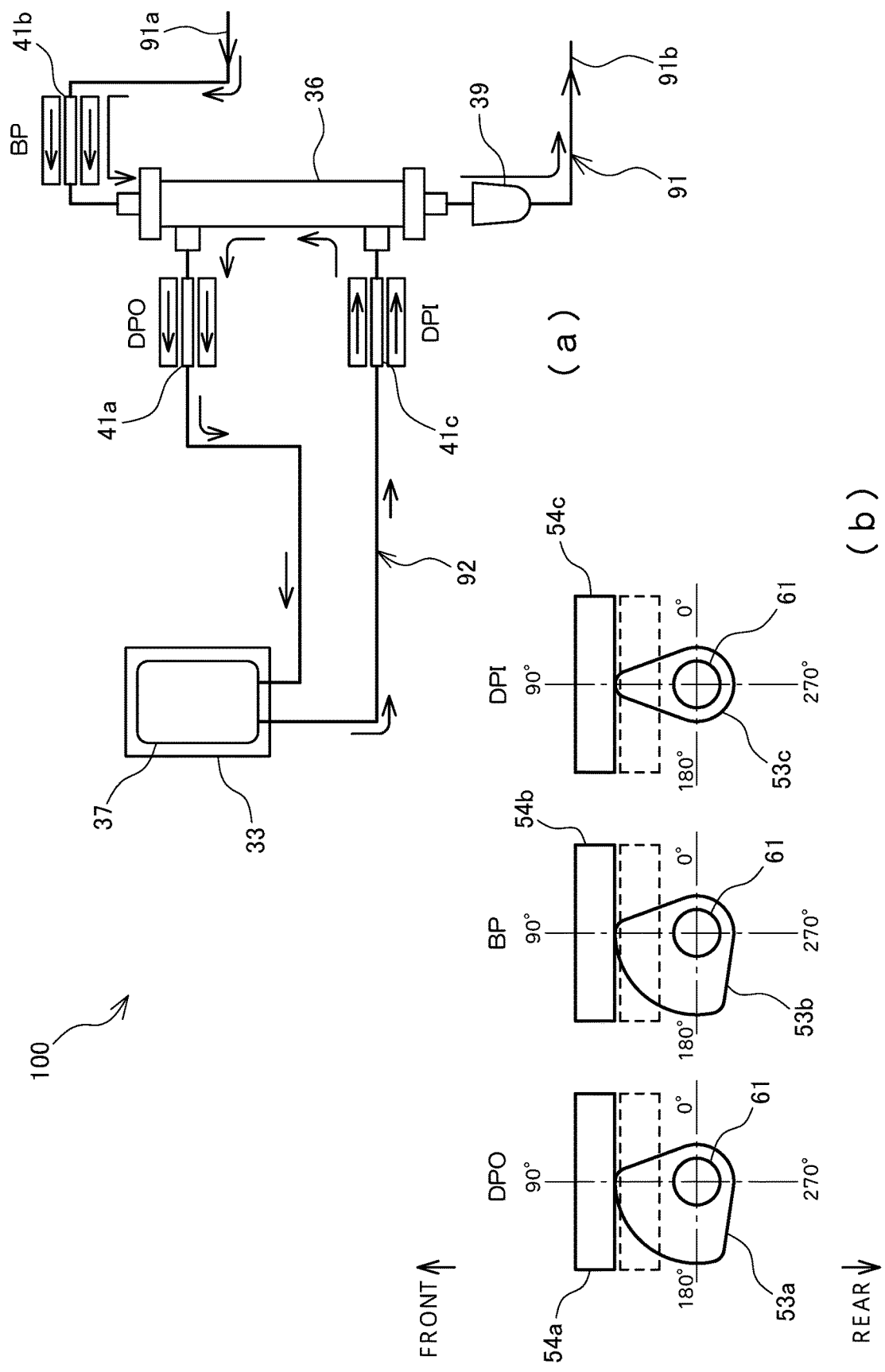
FIG. 7 is an explanatory diagram showing a liquid flow (a) and rotary cam positions (b) in the blood purification device during a dialysis operation.

Further, in the blood purification device 100 of the present embodiment, as described by reference to FIGS. 6(*a*) and 6(*b*), the pump tubes 41*a*-41*c* can be opened and prevented from being subjected to a pressing force while in the stopped state. It is thereby possible to suppress degradation of the pump tubes 41*a*-41*c* due to use.

Furthermore, in the blood purification device 100 of the present embodiment, the opening and closing of the pump tubes 41 (41*a*-41*c*) are carried out by causing the finger driving units 20 (20*a*-20*c*) housed in the device main body 10 to advance and retract with respect to the cover 30 by means of the pump tube opening/closing mechanism 50 housed in the device main body 10. Accordingly, even when the pump tubes 41 (41*a*-41*c*) are arranged in the cover 30 where it is difficult to mount a mechanism for moving the pump tubes 41 (41*a*-41*c*), opening and closing of the liquid circuit can be carried out with a simple configuration.

In the above-described embodiment, the rotary cams 53*a*-53*c* are described as having shapes that can set the open and closed states of the pump tubes 41*a*-41*c* corresponding to the stopped state, the dialysis operation, the priming operation, and the blood pump BP calibration operation of the blood purification device 100. However, the shapes of the rotary cams 53a-53c are not limited thereto, and may also be those that correspond to combinations of open and closed states of the pump tubes 41a-41c required for other operations. For example, when rotation angle positions are assigned at intervals of 90° as in the case of the rotary cams 53a-53c described above, six patterns of rotary cams as shown in FIGS. 10(a) to 10(f) can be obtained. The rotary cam shown in FIG. 10(a) has a pattern for opening a pump tube 41 at all angular positions. The rotary cam shown in FIG. 10(b) has a pattern for closing a pump tube 41 at the 90° position and opening the pump tube 41 at the 0°, 180°, and 270° positions, similar to the rotary cam 53c described above. The rotary cam shown in FIG. 10(c) has a pattern for closing a pump tube 41 at the 90° position and the 180° position and opening the pump tube 41 at the 0° position and the 270° position, similar to the rotary cams 53a and 53b described above. The rotary cam shown in FIG. 10(d) has a pattern for closing a pump tube 41 at the 90° position and the 270° position and opening the pump tube 41 at the 0° position and the 180° position. The rotary cam shown in FIG. 10(e) has a pattern for closing a pump tube 41 at the 90°, 180°, and 270° positions and opening the pump tube 41 at the 0° position. The rotary cam shown in FIG. 10(f) has a pattern for closing a pump tube 41 at all angular positions.

By combining rotary cams of the six patterns shown in FIGS. 10(a) to 10(f), combinations of open and closed states of the pump tubes 41a-41c required for various operations of the blood purification device 100 can be realized. With this arrangement, the blood purification device 100 can be operated in various operation patterns by driving the single motor 60 of the pump tube opening/closing mechanism 50. Here, the assignment interval angle is not limited to 90°, and may alternatively be 45° or 60°, for example. Further, although in the present embodiment a short side of the rotary cam corresponds to an open state and a long side corresponds to a closed state, it is alternatively possible to configure such that, conversely, a short side corresponds to a closed state and a long side corresponds to an open state.

Next, a blood purification device 200 according to another embodiment will be described by reference to FIGS. 11 to 13. Parts equivalent to those of the blood purification device 100 described above by reference to FIGS. 1 to 9 are labeled with the same reference signs, and repeated description thereof will be omitted.

Figure 11:
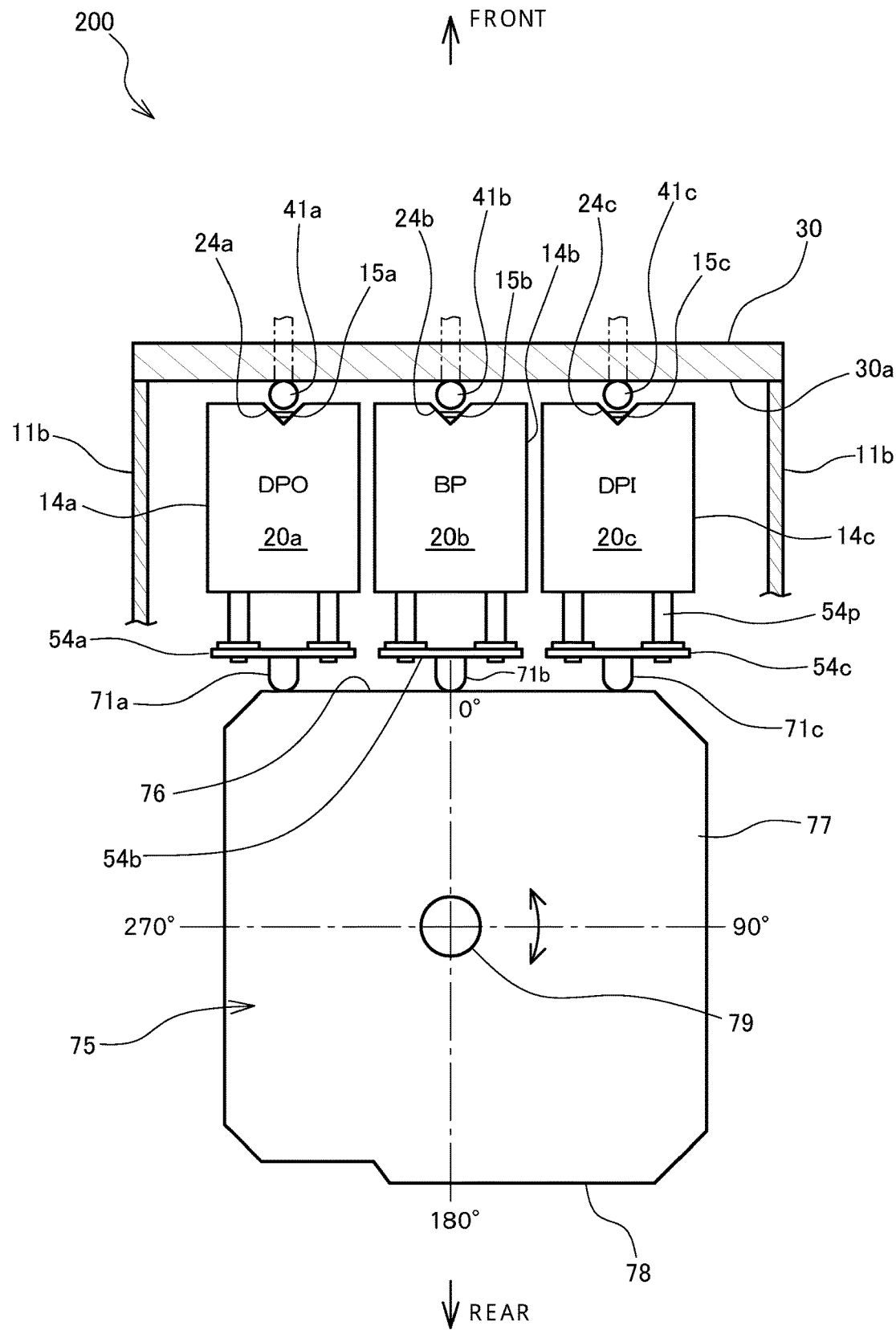
FIG. 11 is a plan sectional view of a blood purification device according to a further embodiment, showing a cam position in the blood purification device in a stopped state.

As shown in FIG. 11, in the blood purification device 200 of the present embodiment, a single rotary cam 75 that is rotated within a horizontal plane by a shaft 79 is used, instead of the three rotary cams 53a-53c of the blood purification device 100, to thereby cause the finger casings 14a-14c to advance and retract with respect to the cover 30. Further, projections 71a-71c that come into contact with the cam surfaces of the rotary cam 75 are provided respectively on the cam followers 54a-54c. The projections 71a-71c are connected to the finger casings 14a-41c via the cam followers 54a-54c and the posts 54p.

Figure 12:
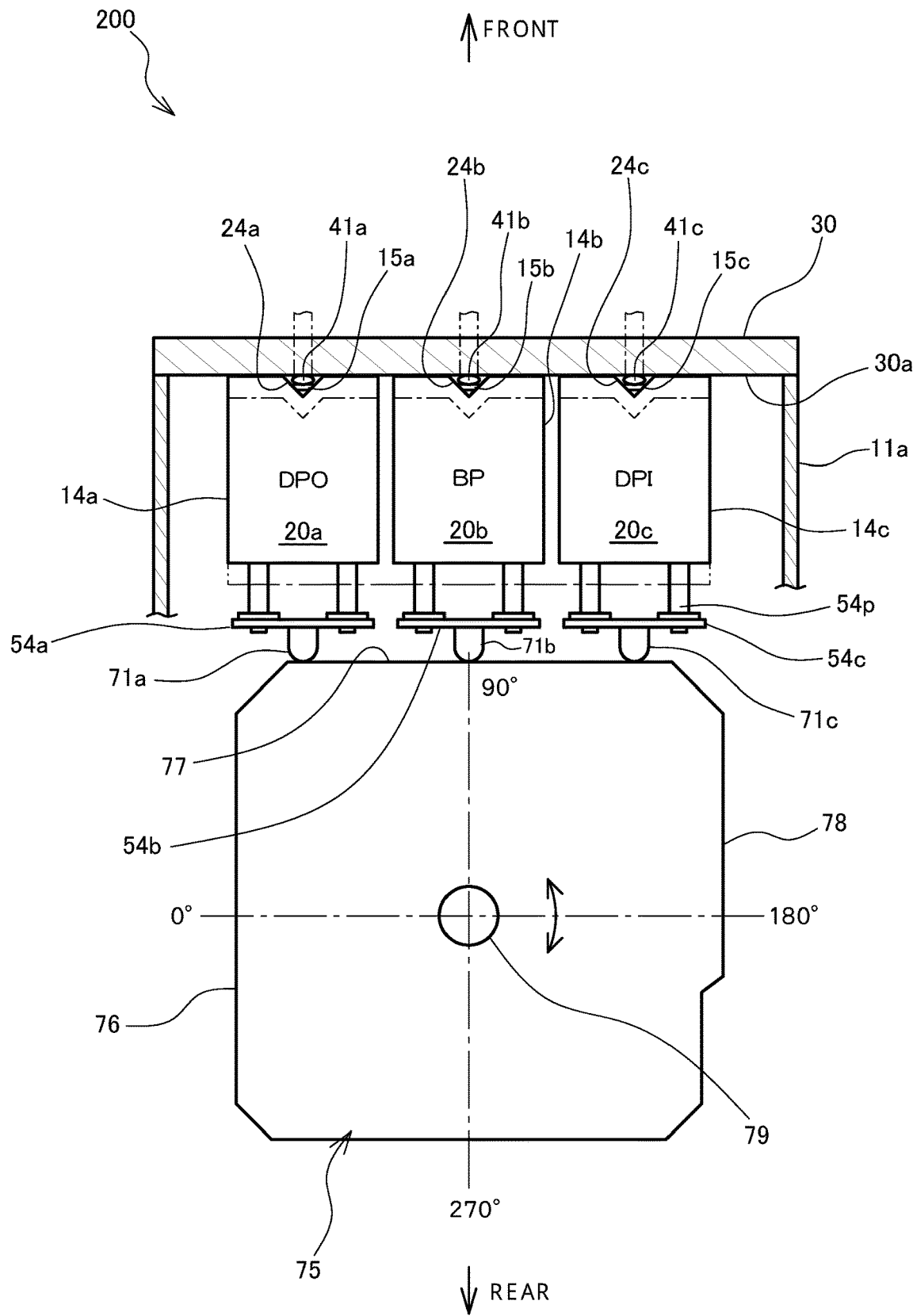
FIG. 12 is a plan sectional view of the blood purification device according to the further embodiment, showing a cam position in the blood purification device during a dialysis operation.
Figure 13:
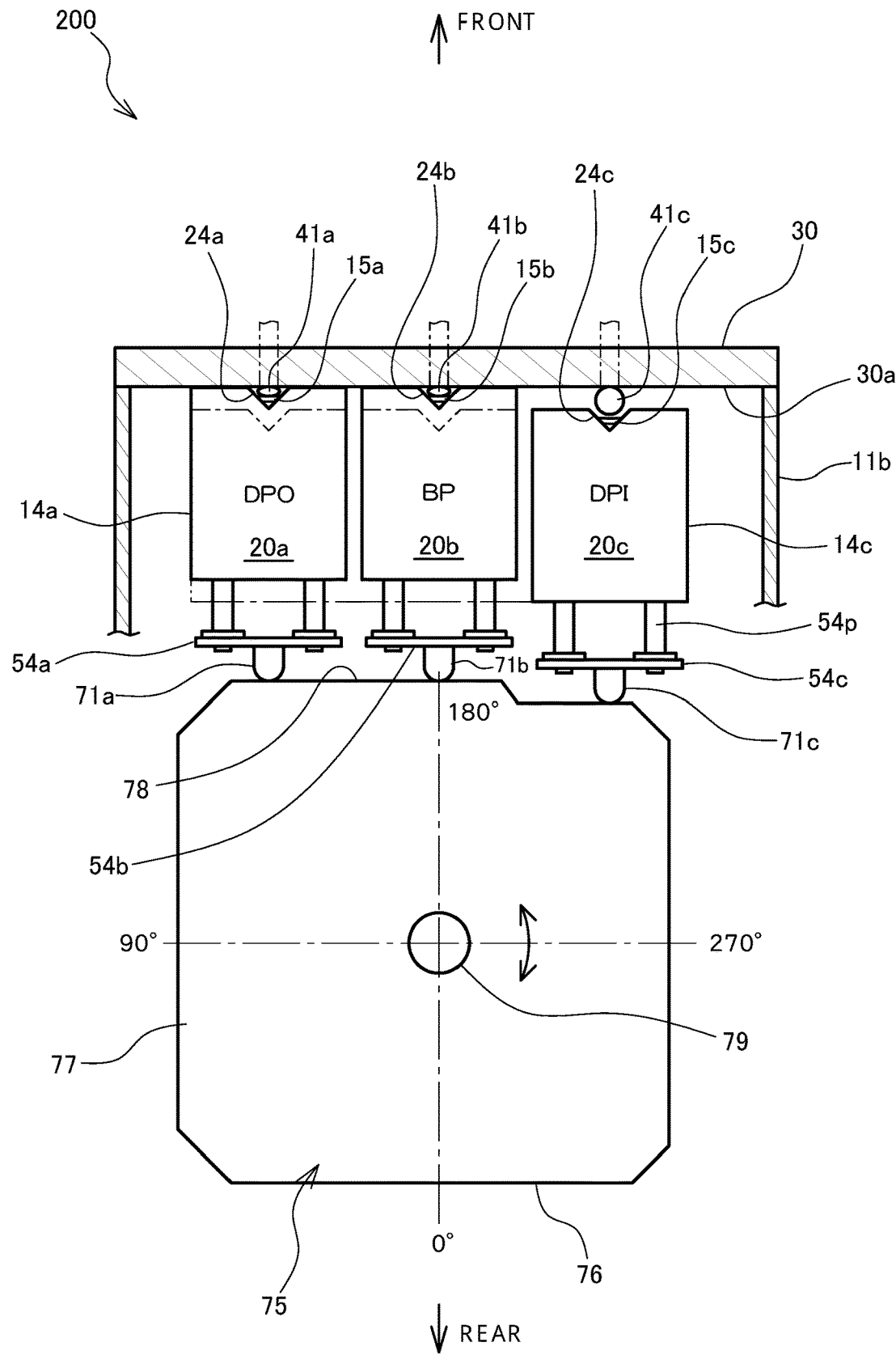
FIG. 13 is a plan sectional view of the blood purification device according to the further embodiment, showing a cam position in the blood purification device during a priming operation or a blood pump calibration operation.

The rotary cam 75 includes: a first cam surface 76 that places the projections 71a-71c connected to the finger casings 14a-41c in the rear open position as shown in FIG. 11; a second cam surface 77 that places the projections 71a-71c in the front closed position as shown in FIG. 12; and a third cam surface 78 that places the projections 71a and 71b in the front closed position and places the projection 71c in the rear open position as shown in FIG. 13. The first cam surface 76 is the 0° position, the second cam surface 77 is the 90° position, and the third cam surface 78 is the 180° position. By rotating the shaft 79, it is possible to set three states; namely: a state in which all of the pump tubes 41a-41c are opened; a state in which all of the pump tubes 41a-41c are closed; and a state in which the pump tubes 41a and 41b are closed and the pump tube 41c is opened.

The blood purification device 200 of the present embodiment achieves the same advantageous effects as the blood purification device 100 described above.

Figure 14:
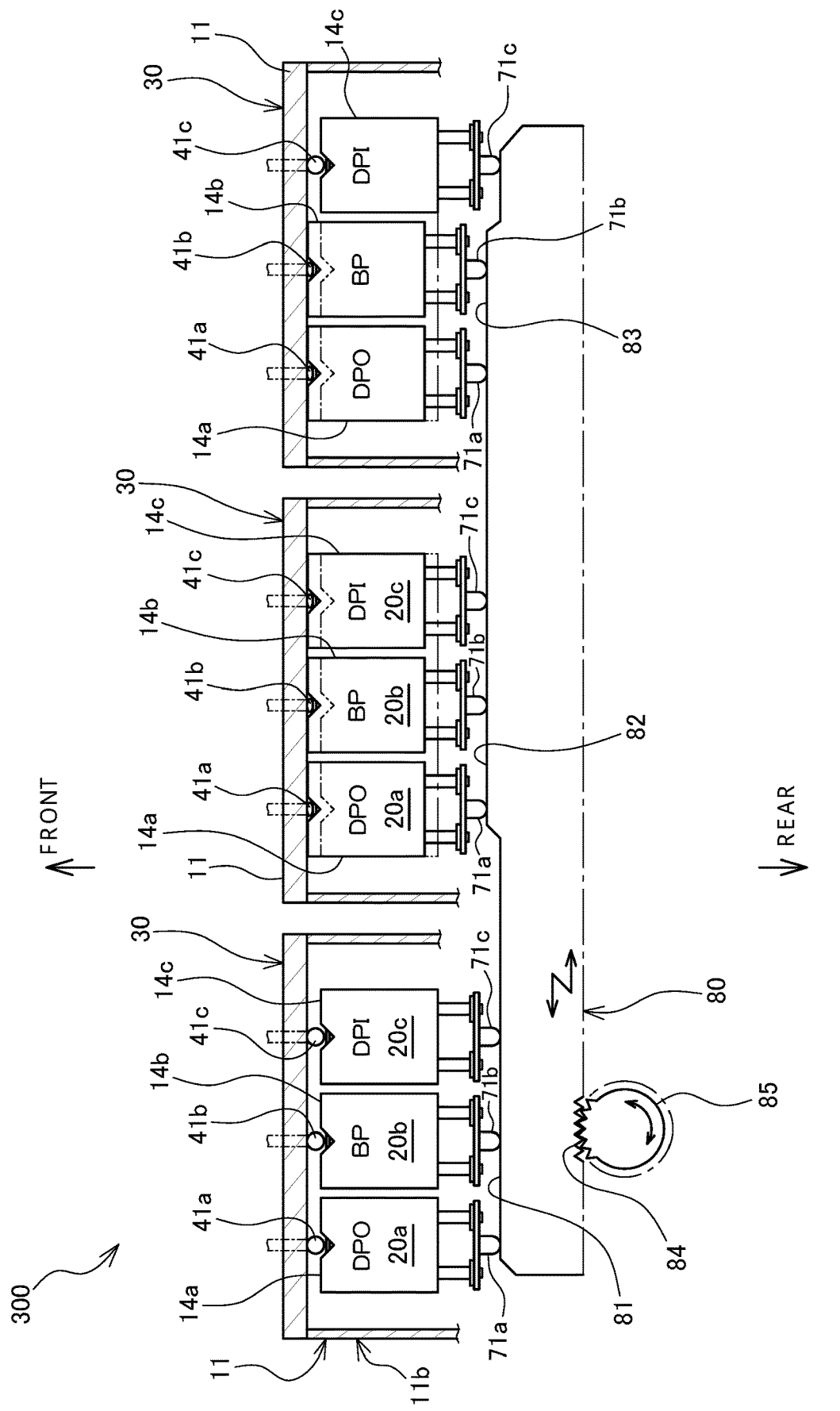
FIG. 14 is a plan sectional view of a blood purification device according to another embodiment, showing cam positions in the blood purification device in a stopped state, during a dialysis operation, and during a priming operation or a blood pump calibration operation.

Next, a blood purification device 300 according to another embodiment will be described by reference to FIG. 14. Parts equivalent to those of the blood purification devices 100 and 200 described above by reference to FIGS. 1 to 13 are labeled with the same reference signs, and repeated description thereof will be omitted. FIG. 14 depicts, in a sequential manner, respective states in which first to third cam surfaces 81, 82, and 83 of a plate cam 80 are located in a central part of the housing 11. In the actual device, when the first cam surface 81 is inside the housing 11, the second cam surface 82 and the third cam surface 83 are located outside the housing 11. When the second cam surface 82 is inside the housing 11, the first cam surface 81 and the third cam surface 83 are located outside the housing 11. When the third cam surface 83 is inside the housing 11, the first cam surface 81 and the second cam surface 82 are located outside the housing 11.

The blood purification device 300 of the present embodiment is configured by replacing the rotary cam 75 of the blood purification device 200 described above by reference to FIGS. 11 to 13 with the linearly-extending plate cam 80. As shown in FIG. 14, the plate cam 80 is moved to the left and the right by rotation of a drive gear 85 in engagement with a gear surface 84.

As shown in FIG. 14, the plate cam 80 comprises: the first cam surface 81 that places the projections 71a-71c in the rear open position; the second cam surface 82 that places the projections 71a-71c in the front closed position as shown in FIG. 12; and the third cam surface 83 that places the projections 71a and 71b in the front closed position and places the projection 71c in the rear open position as shown in FIG. 13. By rotating the drive gear 85 and thereby moving the plate cam 80 in the width direction, it is possible to set three states; namely: a state in which all of the pump tubes 41a-41c are opened; a state in which all of the pump tubes 41a-41c are closed; and a state in which the pump tubes 41a and 41b are closed and the pump tube 41c is opened.

The blood purification device 300 of the present embodiment achieves the same advantageous effects as the blood purification devices 100 and 200 described above.

Next, a blood purification device 400 according to another embodiment will be described by reference to FIGS. 15 and 16. The blood purification device 400 of the present embodiment is configured such that a cassette 130 having a rear plate 32 is detachably mounted thereto, instead of the cover 30 of the blood purification device 100 described by reference to FIGS. 1 to 9. Parts equivalent to those of the blood purification device 100 described above by reference to FIGS. 1 to 9 are labeled with the same reference signs, and repeated description thereof will be omitted.

Figure 15:
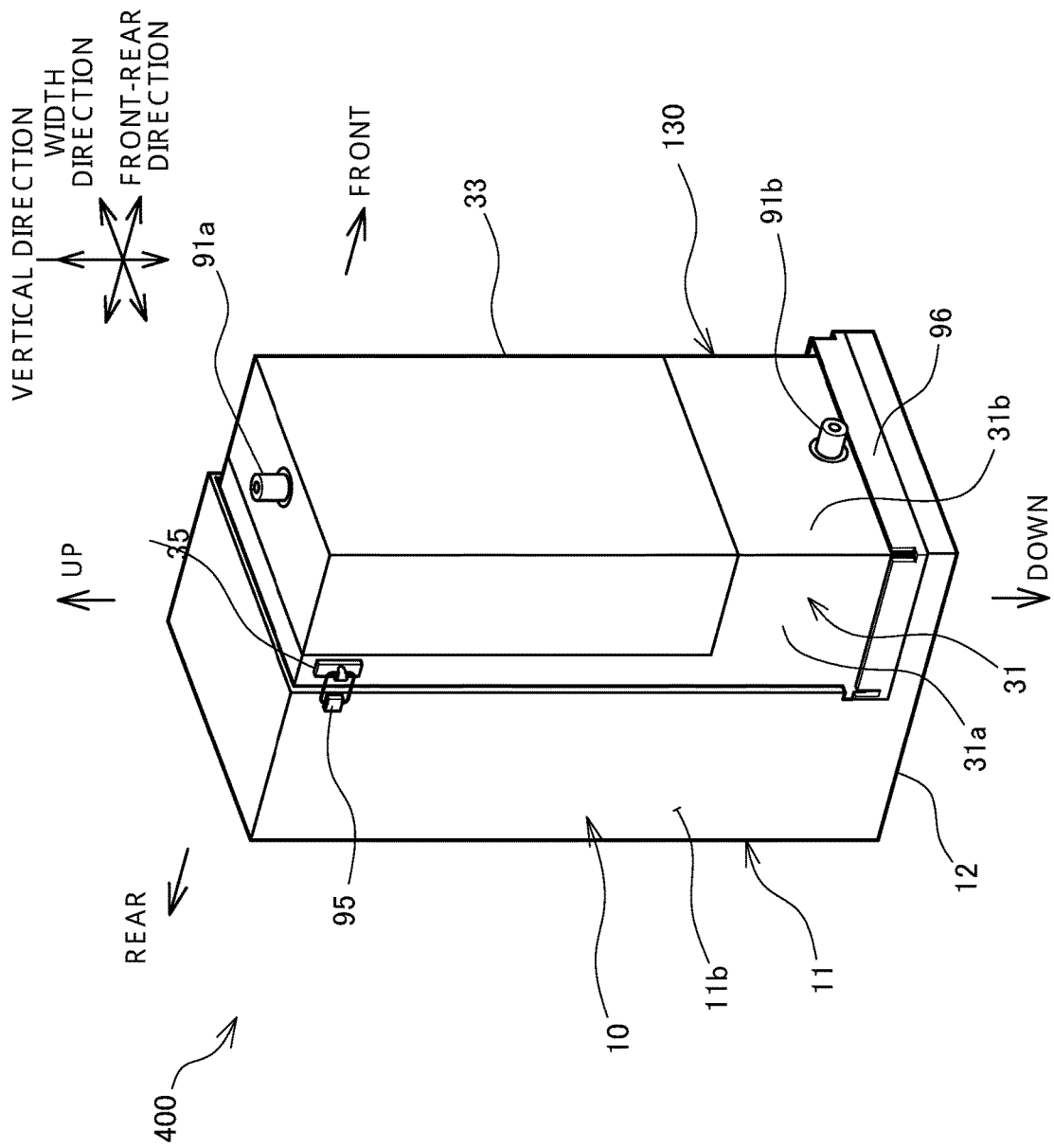
FIG. 15 is a perspective view of a blood purification device according to a further embodiment.

As shown in FIG. 15, the blood purification device 400 comprises the device main body 10, and the cassette 130 that is detachably mounted to the device main body 10. The cassette 130 is mounted to the device main body 10 by fitting its lower part into a cassette receiving seat 96 of the device main body 10, and fastening a hook 35 provided on its upper part with a metal fixture 95 provided on the device main body 10. When being used for dialysis, a blood circuit inlet 91a and a blood circuit outlet 91b of the cassette 130 are respectively connected to blood vessels of a human body so as to carry out dialysis. In the following description, the direction in which the device main body 10 and the cassette 130 are arranged will be referred to as the front-rear direction, the direction orthogonal to the front-rear direction in a horizontal plane will be referred to as the width direction, and the upright direction will be referred to as the vertical direction.

Figure 16:
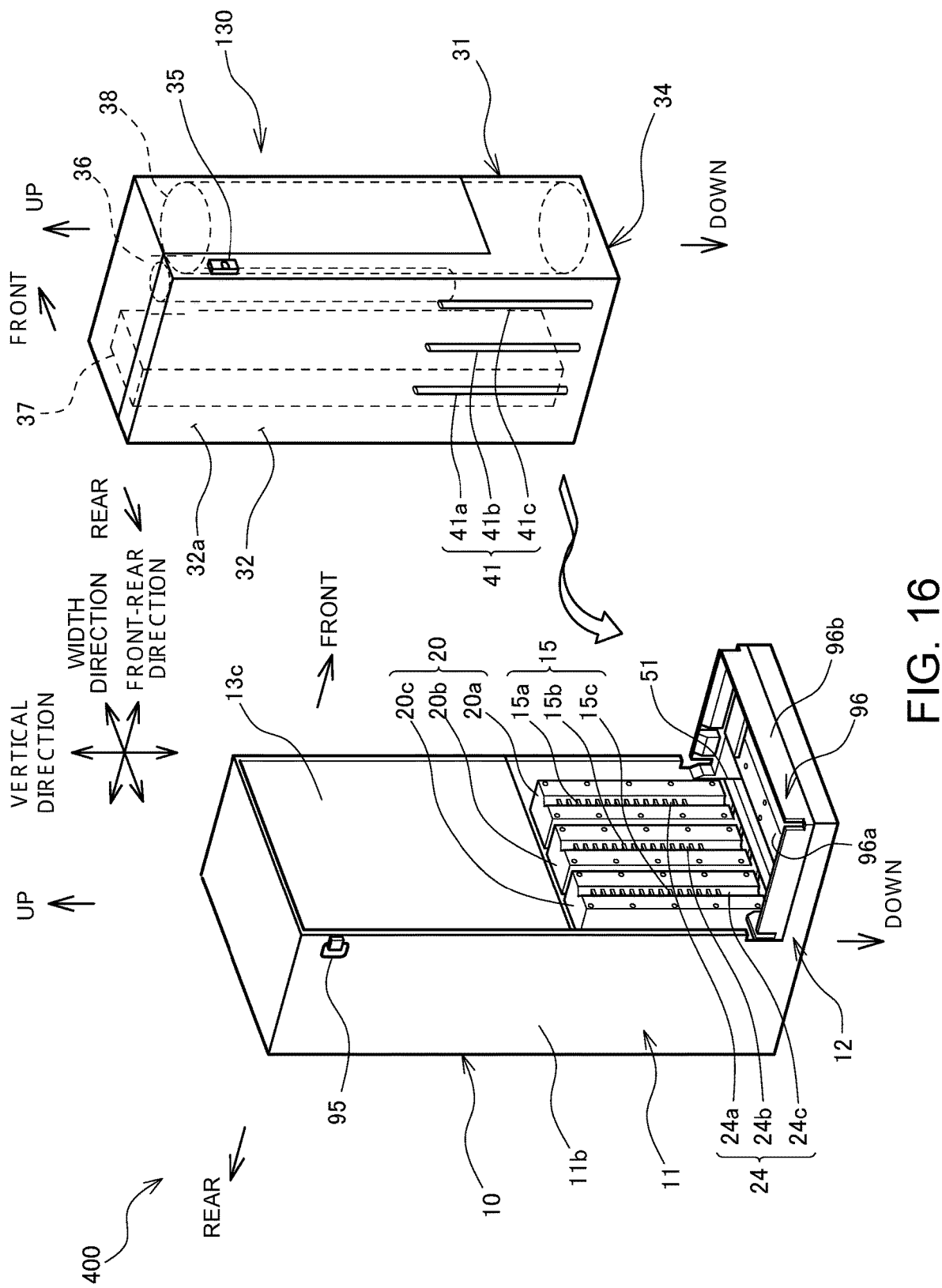
FIG. 16 is an exploded perspective view of the blood purification device according to the further embodiment.

As shown in FIG. 16, a casing 31 of the cassette 130 houses therein the dialyzer 36, the dialysate regeneration column 38, and the water removal container 37. The plurality of elastic pump tubes 41 (41a-41c) are mounted on a surface 32a of the rear plate 32, which is a flat plate of the casing 31 that is located facing the device main body 10. Accordingly, similar to the cover 30 described above, the rear plate 32 of the cassette 130 of the present embodiment constitutes a tube receiving plate that holds the pump tubes 41 (41a-41c). The device main body 10 includes the housing 11, finger driving units 20 received inside the housing 11, the pump tube opening/closing mechanism 50, and the control unit 65. The finger driving units 20, the pump tube opening/closing mechanism 50, and the control unit 65 are identical to those of the blood purification device 100 described above.

The base 12 of the housing 11 extends forward, and the cassette receiving seat 96 is mounted to the extended portion. The cassette receiving seat 96 is formed by providing a flange 96b, into which the cassette 130 is to be fitted, in an upright manner in a cornered C-shape on a peripheral portion of a bottom plate 96a. When the cassette 130 is fitted into the cassette receiving seat 96, a bottom plate 34 of the cassette 130 is supported by the bottom plate 96a of the cassette receiving seat 96, and a lower part of the casing 31 of the cassette 130 fits on the inner side of the flange 96b of the cassette receiving seat 96. When the cassette 130 is mounted to the device main body 10 and the surface 32a of the rear plate 32 of the cassette 130 located toward the device main body 10 is in contact with the front surface of the front plate 13c of the device main body 10, the pump tubes 41 (41a-41c) are received in the vertically-extending V-shaped tube receiving grooves 24 (24a-24c) provided on the front surfaces of the finger casings 14 (14a-14c), in the same manner as described above by reference to FIGS. 3 and 4. The finger driving units 20a-20c and the pump tubes 41a-41c constitute the dialysate outlet pump DPO, the blood pump BP, and the dialysate inlet pump DPI, respectively.

Operation of the blood purification device 400 of the present embodiment is identical to that of the blood purification device 100 described above. In the blood purification device 400 of the present embodiment, the dialyzer 36, the water removal container 37, the dialysate regeneration column 38, the pump tubes 41a-41c, and connection tubes connecting between the respective components, all of which constitute the blood circuit 91 and the dialysate circuit 92, are housed in the cassette 130 as a single unit, and this unit can be mounted to and detached from the device main body 10.

Accordingly, in addition to the advantageous effects achieved by the blood purification device 100, the blood purification device 400 of the present embodiment also achieves the advantageous effects that the cassette 130 integrating the liquid-contacting section can be used in a disposable manner and that the handling of the blood purification device 400 can thereby be simplified.

Figure 17:
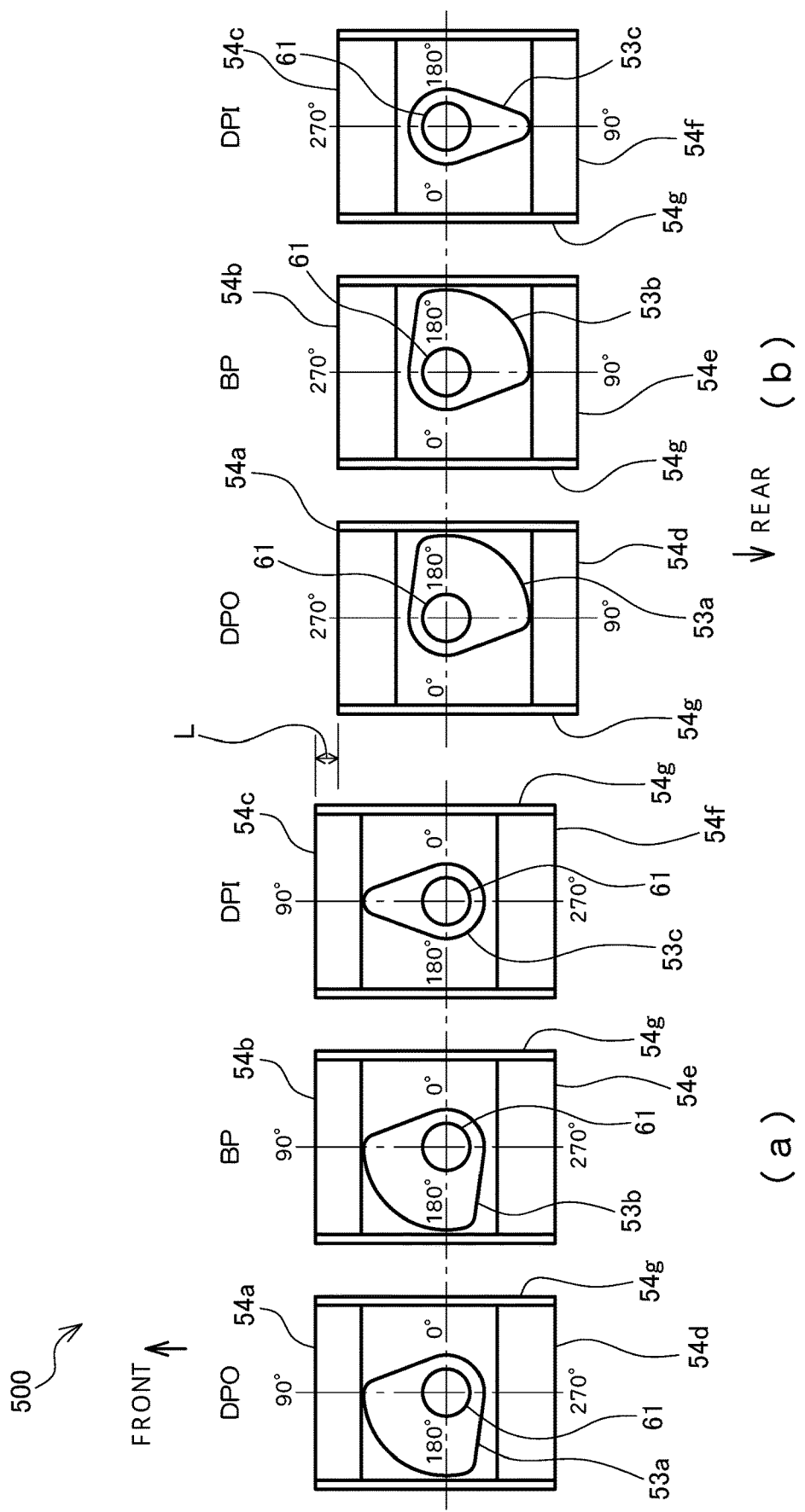
FIG. 17 is an explanatory diagram showing cams and cam followers in a blood purification device according to another embodiment.

Next, a blood purification device 500 according to another embodiment will be described by reference to FIG. 17. The blood purification device 500 of the present embodiment is such that, in addition to the cam followers 54a-54c arranged toward the front of the rotary cams 53a-53c, cam followers 54d-54f are provided toward the rear, and the cam followers 54a-54c are respectively formed into single units with the cam followers 54d-54f by being connected by connecting members 54g. The configurations of the rotary cams 53a-53c and the cam followers 54a-54c are identical to those of the blood purification device 100 described above by reference to FIGS. 1 to 9. Here, the blood purification device 500 does not include the coil springs 52. The rotary cams 53a-53c, the cam followers 54a-54c and 54d-54f, and the connecting members 54g constitute the retraction mechanism.

As shown in FIG. 17(a), when the shaft 61 is rotated by 90° from the initial position, the rotary cams 53a-53c push the front cam followers 54a-54c forward into the front closed position. As a result, the finger casings 14a-14c are moved forward, and the fingers 15a-15c press the pump tubes 41a-41c against the cover 30, so that the dialysate outlet pump DPO, the blood pump BP, and the dialysate inlet pump DPI are placed in a state capable of delivering liquid.

As shown in FIG. 17(b), when the shaft 61 is rotated by 180° from the state shown in FIG. 17(a), the rotary cams 53a-53c push the rear cam followers 54d-54f rearward into the rear open position. As a result, the finger casings 14a-14c are moved rearward by distance L, and the fingers 15a-15c of the dialysate outlet pump DPO, the blood pump BP, and the dialysate inlet pump DPI are placed in a state of being away from the respective pump tubes 41a-41c.

In this way, in the blood purification device 500 of the present embodiment, the finger casings 14a-14b are moved in the front-rear direction by engaging the two front and rear cam followers 54a-54c and 54d-54f with the respective rotary cams 53a-53b, without using the coil springs 52. The blood purification device 500 of the present embodiment achieves the same advantageous effects as the blood purification device 100 described above.

Next, a blood purification device 600 according to another embodiment will be described by reference to FIG. 18. The blood purification device 600 of the present embodiment is configured by providing a flat-shaped tube receiving plate 140 between the cover 30 and the pump tubes 41 (41a-41c). By rotating rotary cams 53d attached to the shaft 61, the tube receiving plate 140 is caused to advance toward the finger driving units 20 (20a-20c). Further, the tube receiving plate 140 is pulled back toward the cover 30 by coil springs 152 so as to be retracted from the finger driving units 20 (20a-20c). In the blood purification device 600, the finger driving units 20 (20a-20c) are fixed to the device main body 10, and do not move in the front-rear direction.

Figure 18:
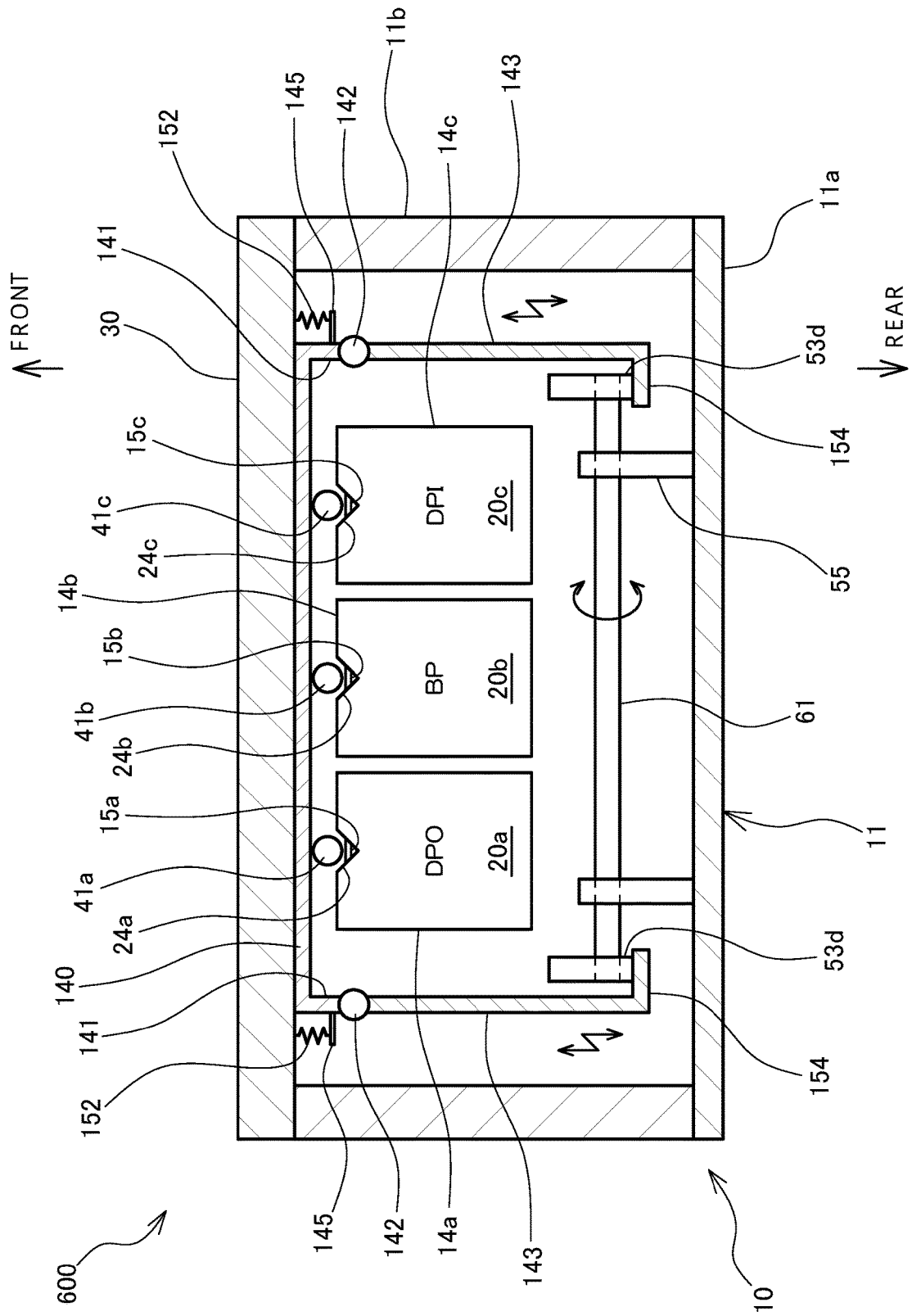
FIG. 18 is a plan sectional view of a blood purification device according to another embodiment.

As shown in FIG. 18, the tube receiving plate 140 is a flat-shaped member disposed between the cover 30 and the pump tubes 41 (41a-41c), and has sufficient hardness for collapsing the pump tubes 41 (41a-41c) in cooperation with the fingers 15a-15c. The vertical length of the tube receiving plate 140 is the same as the vertical length of the fingers 15a-15c. The tube receiving plate 140 is held on the cover 30 together with the pump tubes 41 (41a-41c).

At both ends, in the width direction, of the tube receiving plate 140, flanges 141 are provided extending rearward. At the rear ends of the flanges 141, connection mechanisms 142 are attached, which, when the cover 30 is closed, engage with cam arms 143 mounted to the housing 11. A rib 145 protrudes from a side surface of each flange 141, and the coil spring 152 is attached between the rib 145 and the cover 30.

On the rear plate 11a of the device main body 10, the brackets 55 are attached, which rotatably support the shaft 61. The rotary cams 53d are attached to the two ends of the shaft 61. Further, toward both sides in the interior of the housing 11, the cam arms 143 supported to be slidable in the front-rear direction are mounted. At the rear ends of the cam arms 143, cam followers 154 that engage the rotary cams 53*d* are attached. Each rotary cam 53*d* has at least one protruded part, and may have, for example, the same shape as the rotary cam 53*a* or the rotary cam 53*c* shown in FIG. 6(*b*).

When the cover 30 is closed, the flanges 141 of the tube receiving plate 140 and the cam arms 143 are connected by the connection mechanisms 142. When the shaft 61 is rotated by the motor 60 (not shown), the protruded parts of the rotary cams 53*d* engage the cam followers 154 and move the cam followers 154 rearward. As a result, the tube receiving plate 140 is moved rearward, and the pump tubes 41*a*-41*c* are pressed by the fingers 15*a*-15*c*, so that the dialysate outlet pump DPO, the blood pump BP, and the dialysate inlet pump DPI are placed in a state capable of delivering liquid.

When the shaft 61 is rotated by the motor 60 and the protruded parts of the rotary cams 53*d* are disengaged from the cam followers 154, the tube receiving plate 140 is pulled back toward the cover 30 by the coil springs 152, so that the fingers 15*a*-15*c* of the dialysate outlet pump DPO, the blood pump BP, and the dialysate inlet pump DPI are placed in a state of being away from the pump tubes 41*a*-41*c*.

Although it has been explained that the tube pressing members are the fingers 15 (15*a*-15*c*) in the blood purification devices 100, 200, 300, 400, 500, and 600 of the above-described embodiments, the tube pressing members are not limited thereto, and may alternatively be rollers that squeeze the pump tubes 41 (41*a*-41*c*). When such rollers are used, the surface 30*a* of the cover 30 located toward the device main body 10 and the surface of the tube receiving plate 140 located toward the device main body 10 are configured as a curved surface that conforms to the shape of the outer surface of the rollers.

Next, a blood purification device 110 according to another embodiment will be described by reference to FIGS. 19-24. Parts equivalent to those of the blood purification device 100 described above by reference to FIGS. 1-9 are labeled with the same reference signs, and repeated description thereof will be omitted.

Figure 19:
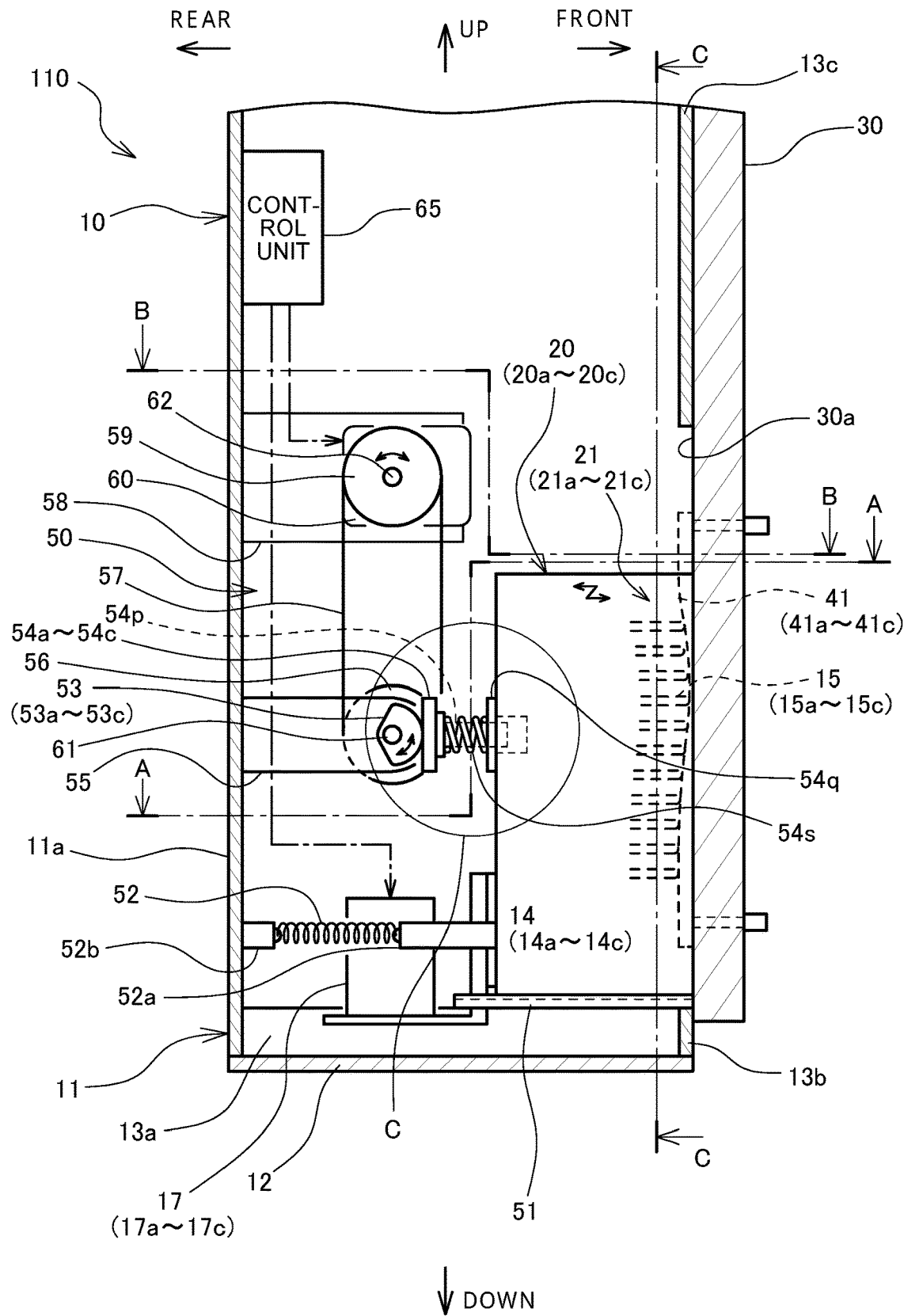
FIG. 19 is an elevational sectional view of a blood purification device according to a further embodiment.
Figure 20:
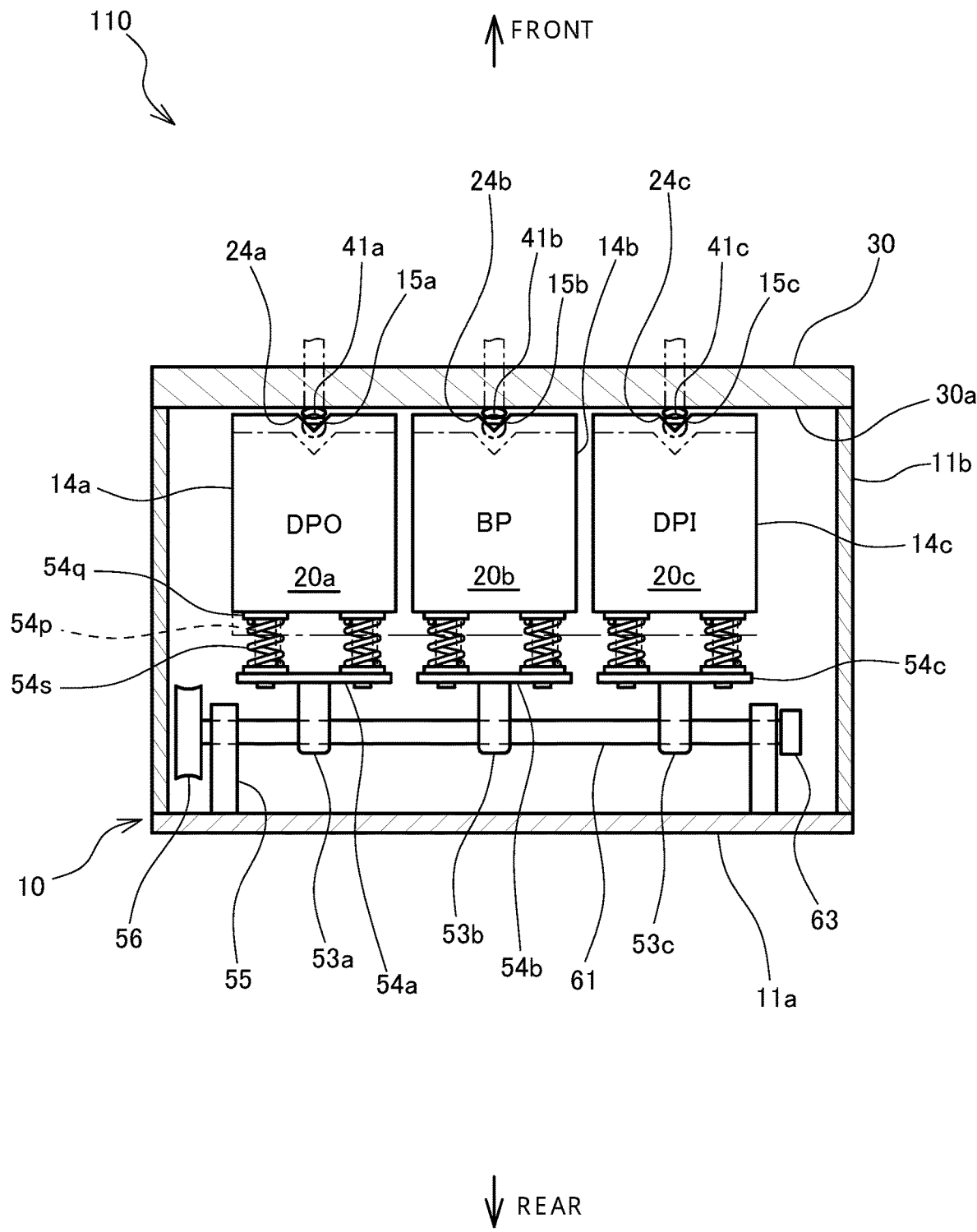
FIG. 20 is a plan sectional view of the blood purification device shown in FIG. 19.

As shown in FIGS. 19 and 20, the blood purification device 110 is configured by attaching the cam followers 54*a*-54*c* to the finger casings 14 (14*a*-14*c*) of the finger driving units 20 (20*a*-20*c*) via adjustment springs 54*s*, which are elastic members. Other structures are identical to those of the blood purification device 100 described above by reference to FIGS. 1 to 9.

Figure 21:
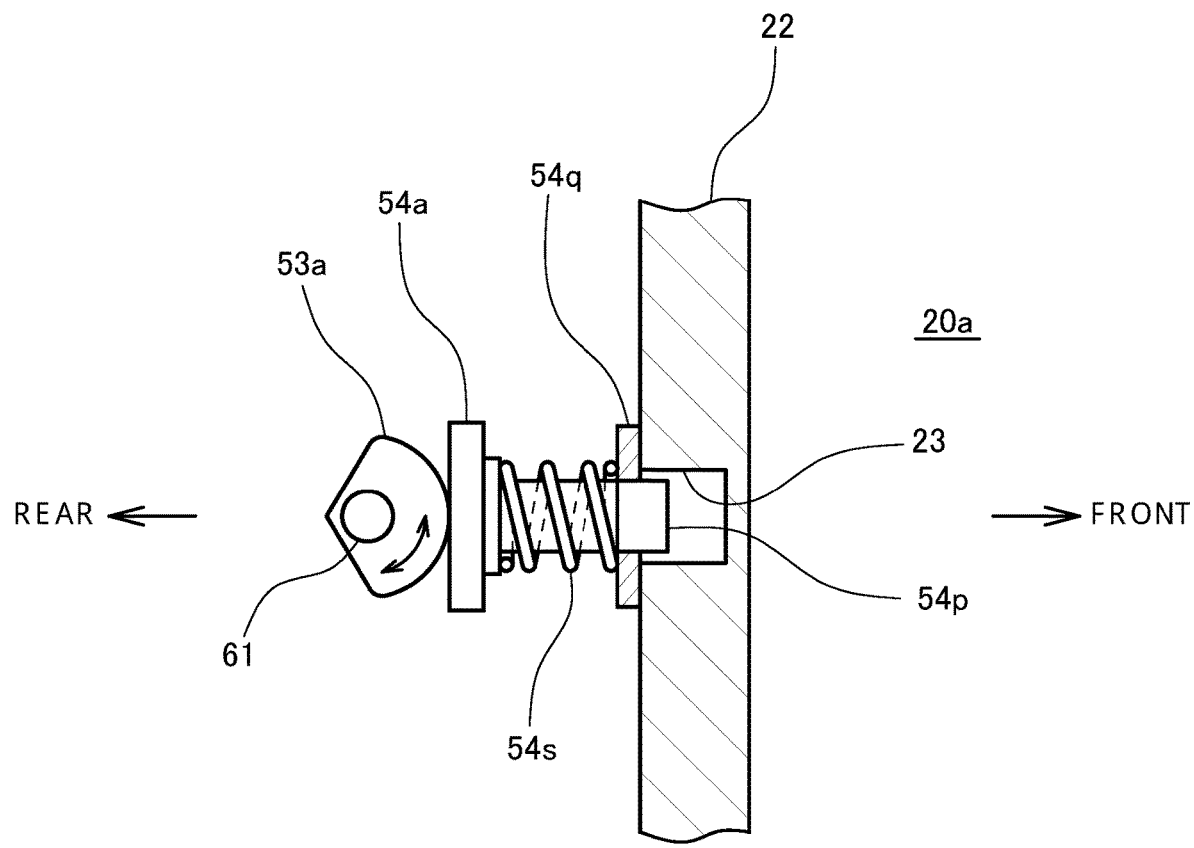
FIG. 21 is an enlarged sectional view of portion C shown in FIG. 19.

As shown in FIG. 21, a post 54*p* is fixed to a front part of the cam follower 54*a*, and a recess 23 into which the tip of the post 54*p* is inserted is formed in the back plate 22 of the finger casing 14*a*. Further, a washer 54*q* having an inner diameter substantially equal to the diameter of the post 54*p* is fixed to the peripheral edge of the recess 23 in the back plate 22. An adjustment spring 54*s* is mounted to the outer periphery of the post 54*p* between the washer 54*q* and the cam follower 54*a*. Although the adjustment spring 54*s* is a coil spring in the blood purification device 110, the adjustment spring 54*s* is not limited thereto, and may alternatively be a leaf spring or may comprise a rubber member. The washer 54*q* may alternatively be not provided.

The rotary cam 53*a* is rotated so as to cause the cam follower 54*a* to advance toward the finger driving unit 20*a*. When the adjustment spring 54*s* is thereby contracted, the tip of the post 54*p* enters into the recess 23 in the back plate 22.

The spring constant of the adjustment spring 54*s* is greater than the spring constant in the direction in which the pump tubes 41 (41*a*-41*c*) are collapsed, is equal to or greater than a spring constant at which the pump tubes 41 (41*a*-41*c*) can be completely closed by the reaction force, and is such that, even when the spring 54*s* is compressed, the reaction force does not damage the pump tubes 41 (41*a*-41*c*).

Figure 22:
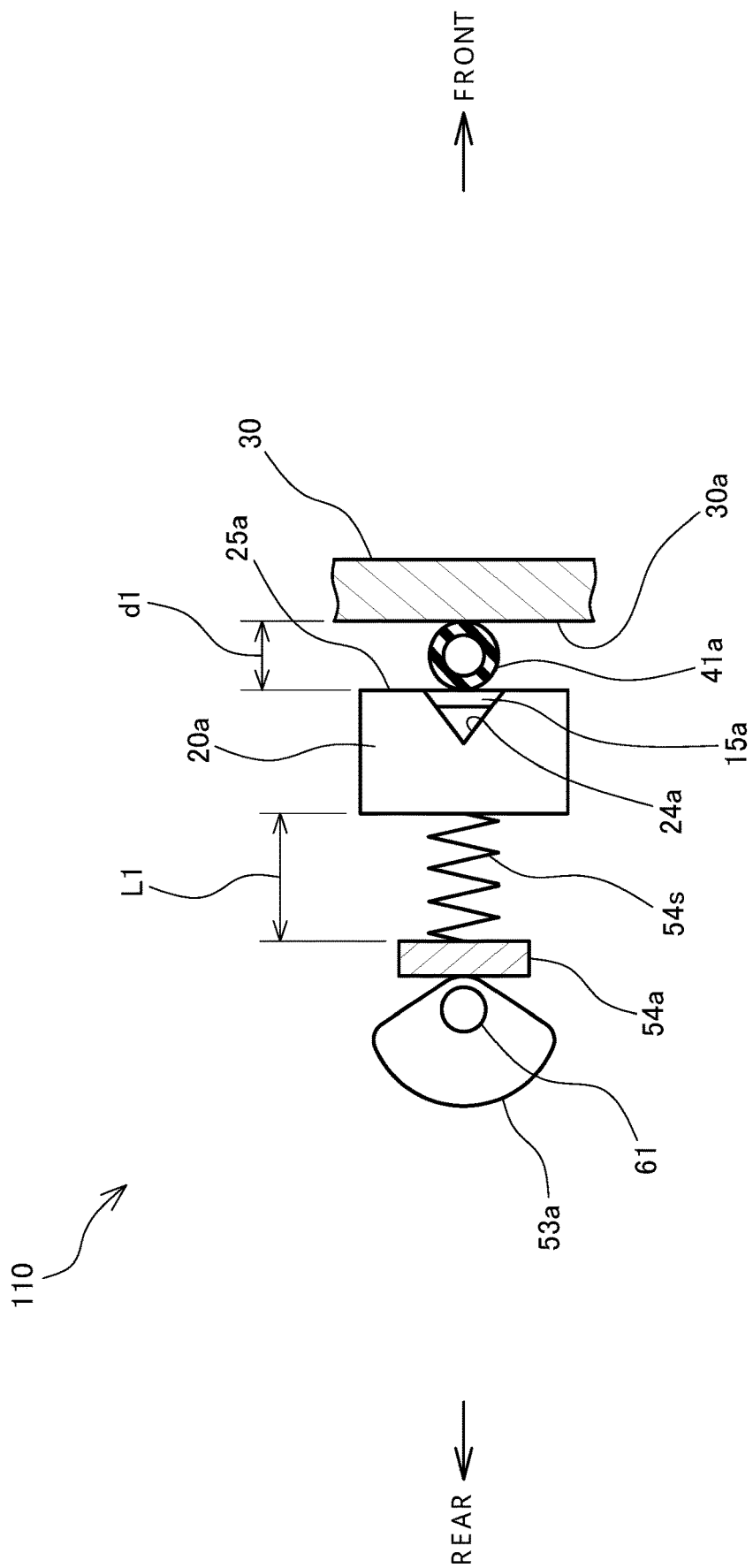
FIG. 22 is a schematic diagram illustrating an initial state of a pump tube closing operation of the blood purification device shown in FIG. 19.
Figure 23:
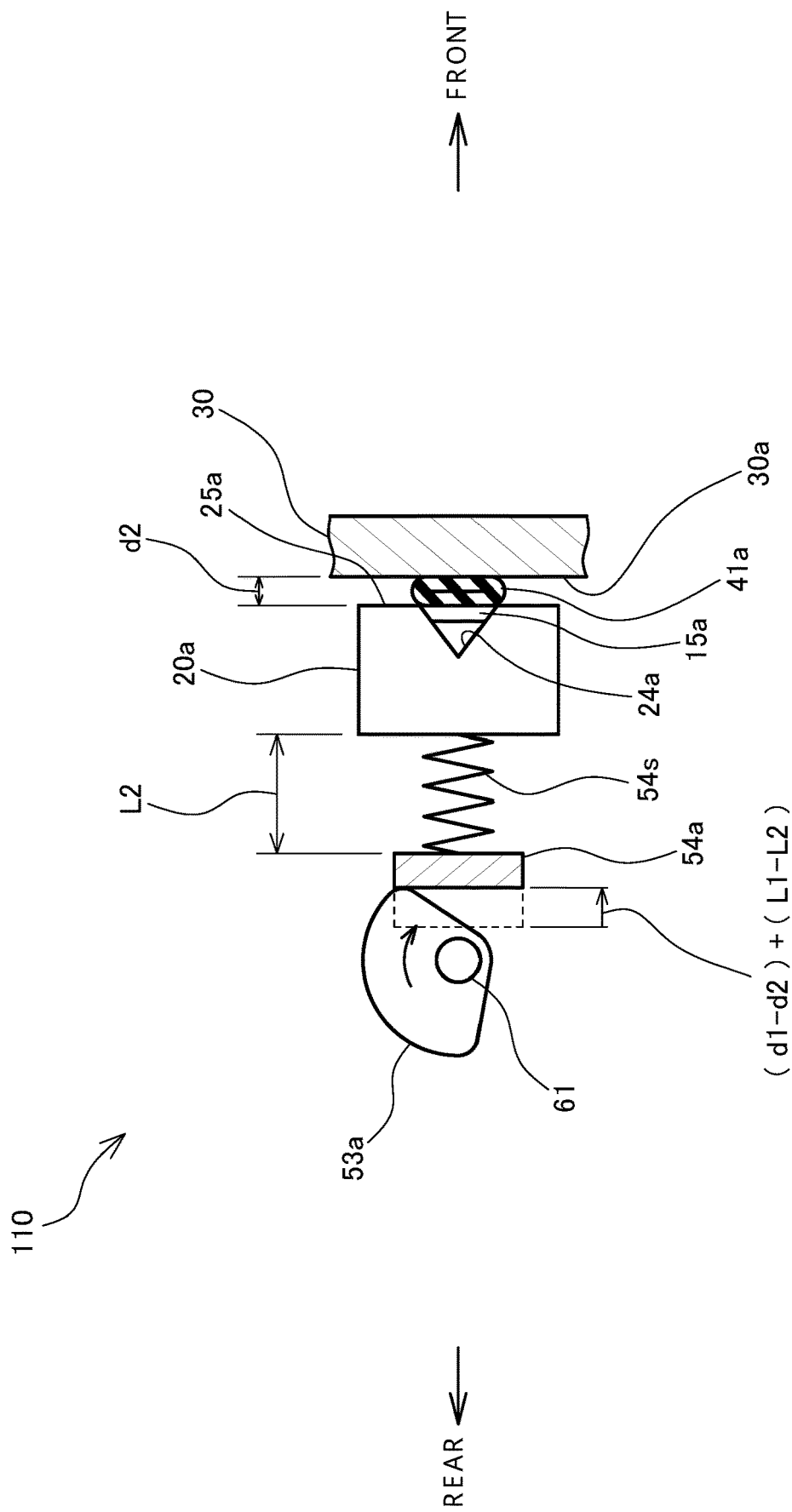
FIG. 23 is a schematic diagram illustrating a state in which the pump tube is collapsed during the pump tube closing operation of the blood purification device shown in FIG. 19.
Figure 24:
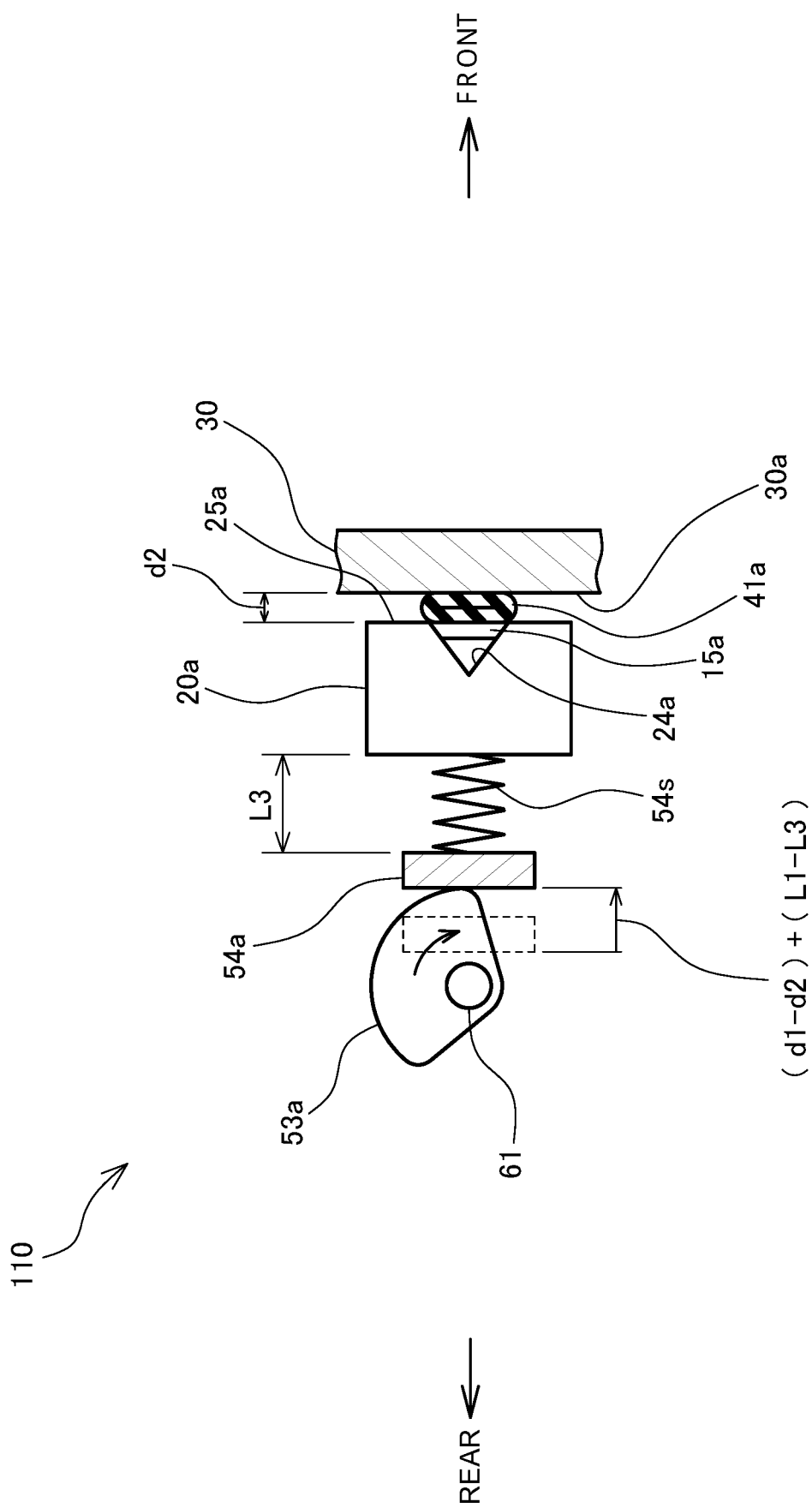
FIG. 24 is a schematic diagram illustrating a state in which an adjustment spring has contracted during the pump tube closing operation of the blood purification device shown in FIG. 19.

A closing operation for closing the pump tube 41*a* by rotating the rotary cam 53*a* of the blood purification device 110 and thereby causing the finger driving unit 20*a* to advance toward the cover 30 will be described by reference to FIGS. 22-24. FIGS. 22-24 are schematic diagrams for explaining the closing operation, and elements shown therein are depicted in a simplified manner. The operation of the finger driving units 20*b* and 20*c* is identical to the operation of the finger driving unit 20*a*.

As shown in FIG. 22, in the initial state, the adjustment spring 54*s* has a reference length L1, and the outer shape of the pump tube 41*a* has a size d1.

As shown in FIG. 23, when the rotary cam 53*a* is rotated, the cam follower 54*a* advances toward the cover 30. As explained above, the spring constant of the adjustment spring 54*s* is greater than the spring constant in the direction in which the pump tube 41*a* is collapsed. Accordingly, when the cam follower 54*a* advances toward the cover 30, the pump tube 41*a* becomes collapsed by being squeezed between the finger 15*a* and the cover 30. When the rotary cam 53*a* has rotated and the pump tube 41*a* is collapsed and placed in the closed state, the pump tube 41*a* has a thickness d2. At that point, the cam follower 54*a* has advanced by (d1-d2)+(L1-L2), and the adjustment spring 54*s* has a length L2 that is slightly reduced from the reference length L1.

Next, as shown in FIG. 24, when the rotary cam 53*a* is rotated further and the cam follower 54*a* advances further toward the cover 30, the adjustment spring 54*s* starts to contract from the length L2 while the thickness of the pump tube 41*a* remains d2. At that time, the tip of the post 54*p* advances into the recess 23 in the back plate 22 shown in FIG. 21. Subsequently, when the rotary cam 53*a* is rotated further and the cam follower 54*a* advances by (d1-d2)+(L1-L3), the adjustment spring 54*s* contracts to a length L3. At that point, there is a gap between the finger driving unit 20*a* and the surface 30*a* of the cover 30. The reaction force of the adjustment spring 54*s* at that time is of a magnitude that does not damage the pump tube 41*a*.

In this way, in the blood purification device 110, after the finger 15*a* has closed the pump tube 41*a*, the adjustment spring 54*s* contracts by a length (L2-L3) and thereby absorbs an advancing distance of the cam follower 54*a*. For this reason, closing and opening of the pump tube 41*a* can be carried out reliably without adjustment of the advancing distance of the finger driving unit 20*a* with respect to the cover 30 with high accuracy. In addition, since the reaction force of the adjustment spring 54*s* upon contracting to the length L3 is of a magnitude that does not damage the pump tube 41*a*, excessive pressing of the pump tube 41*a* can be avoided, and damages to the pump tube 41*a* can be suppressed.

Although it is explained above that the recess 23 into which the tip of the post 54*p* is inserted is provided in the back plate 22 of the finger casing 14*a*, the recess 23 may be not provided so long as the structure is such that the tip of the post 54*p* does not interfere with the back plate 22 when the adjustment spring 54*s* is in the contracted state. For example, it may be configured such that the thickness of the washer 54q is greater than the extent of contraction of the adjustment spring 54s, so that the tip of the post 54p advances into the washer 54q when the adjustment spring 54s contracts. Further, the portion of the back plate 22 abutted by the adjustment spring 54s may be formed in a protruded shape.

Figure 25:
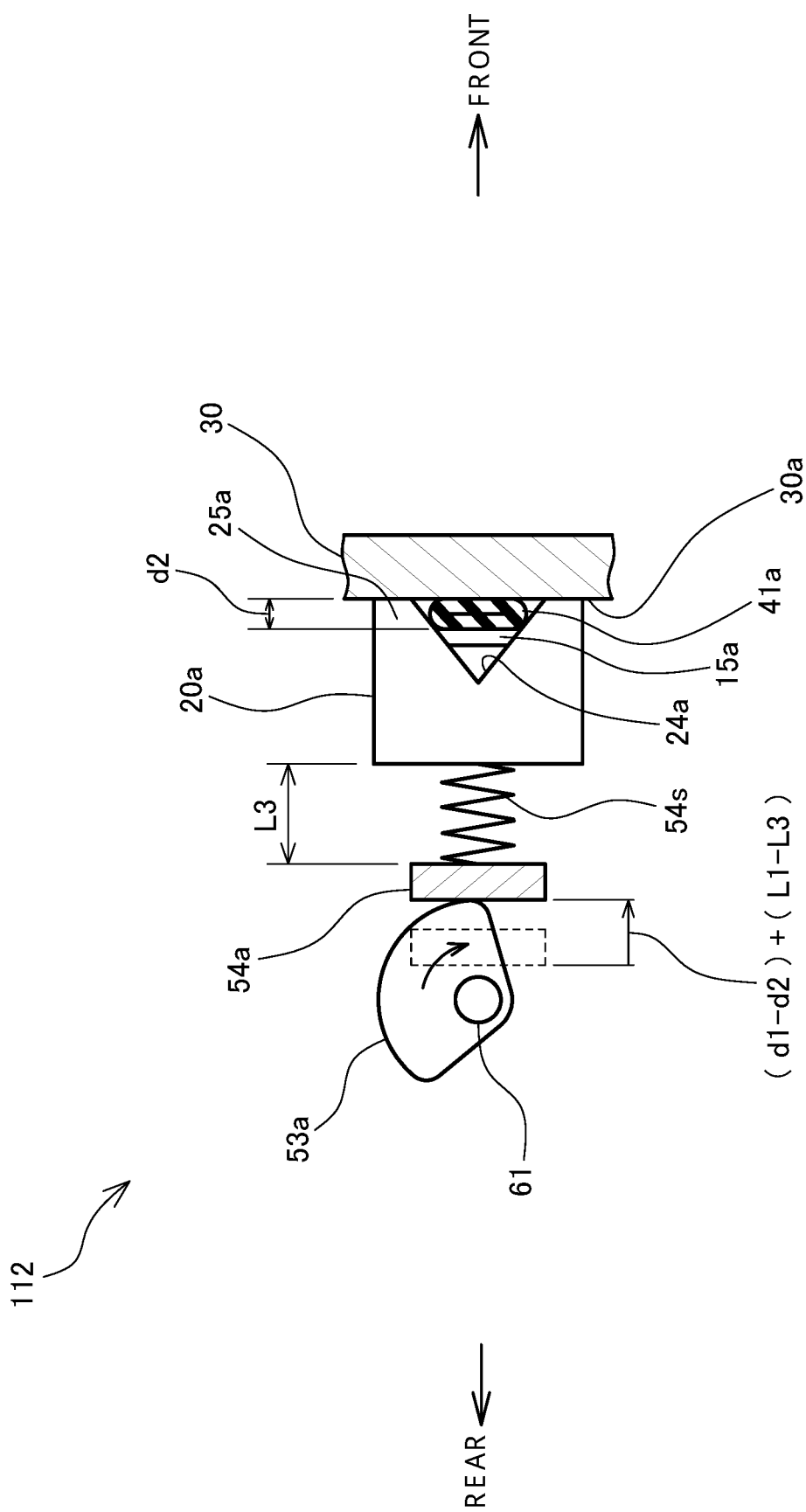
FIG. 25 is a schematic diagram illustrating a state in which an adjustment spring has contracted in a variant of the blood purification device shown in FIG. 19.

Next, a blood purification device 112, which is a variant of the blood purification device 110, will be described by reference to FIG. 25. As shown in FIG. 25, the blood purification device 112 is configured such that, in a state where the finger 15a has moved to the frontmost position, the front end of the finger 15a is located rearward by a distance d2 from the front end 25a of the finger driving unit 20a. The configuration of the finger driving units 20b and 20c is the same as that of the finger driving unit 20a. Other structures are identical to those of the blood purification device 110 described above with reference to FIGS. 19-24.

According to this configuration, as shown in FIG. 25, when the finger 15a closes the pump tube 41a and the thickness of the pump tube 41a becomes d2, the front end 25a of the finger driving unit 20a abuts the surface 30a of the cover 30, and the finger 15a does not press the pump tube 41a any further. With this arrangement, it is possible to prevent application of an excessive pressing force to the pump tube 41a, and damages to the pump tube 41a can be more effectively suppressed.

Figure 26:
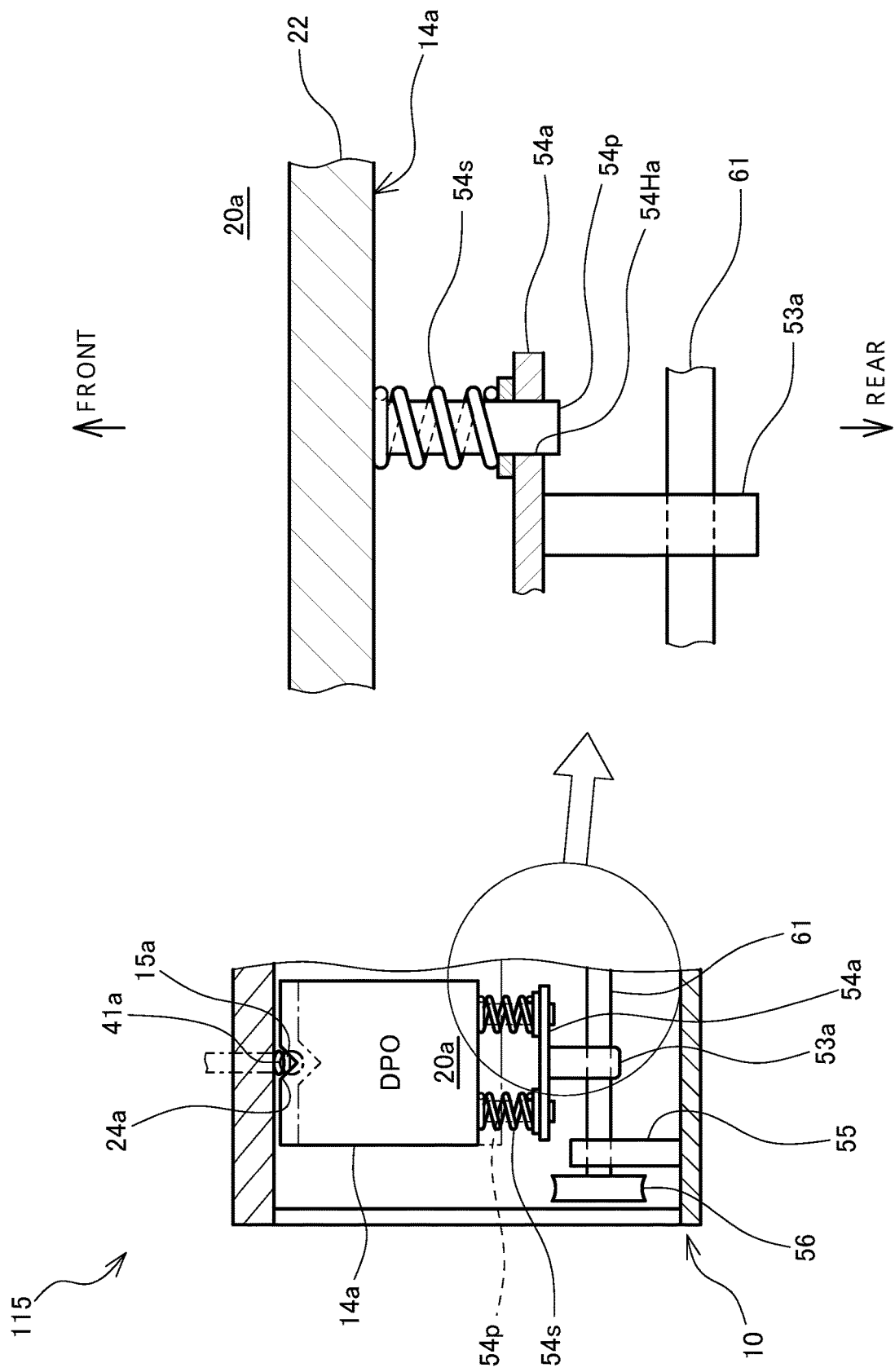
FIG. 26 is a plan sectional view of a blood purification device according to another embodiment.

Next, a blood purification device 115, which is a variant of the blood purification device 110, will be described by reference to FIG. 26. As shown in FIG. 26, in the blood purification device 115, the post 54p is fixed to the back plate 22 of the finger casing 14a, and the cam follower 54a has formed therein a through hole 54Ha which is penetrated by the post 54p. The adjustment spring 54s is mounted around the post 54p between the back plate 22 and the cam follower 54a. When the rotary cam 53 pushes the cam follower 54a forward and the adjustment spring 54s contracts, the rear end of the post 54p advances rearward through the through hole 54Ha in the cam follower 54a. The configurations of the back plates 22 of the finger casings 14b and 14c, the cam followers 54b and 54c, and the posts 54p are the same as those described above.

The blood purification device 115 is identical in operation to that of the blood purification device 110 described above, and achieves the same advantageous effects.

Next, a blood purification device 120 according to another embodiment will be described by reference to FIGS. 27-31. Parts equivalent to those of the blood purification device 100 described above by reference to FIGS. 1-9 are labeled with the same reference signs, and repeated description thereof will be omitted.

Figure 27:
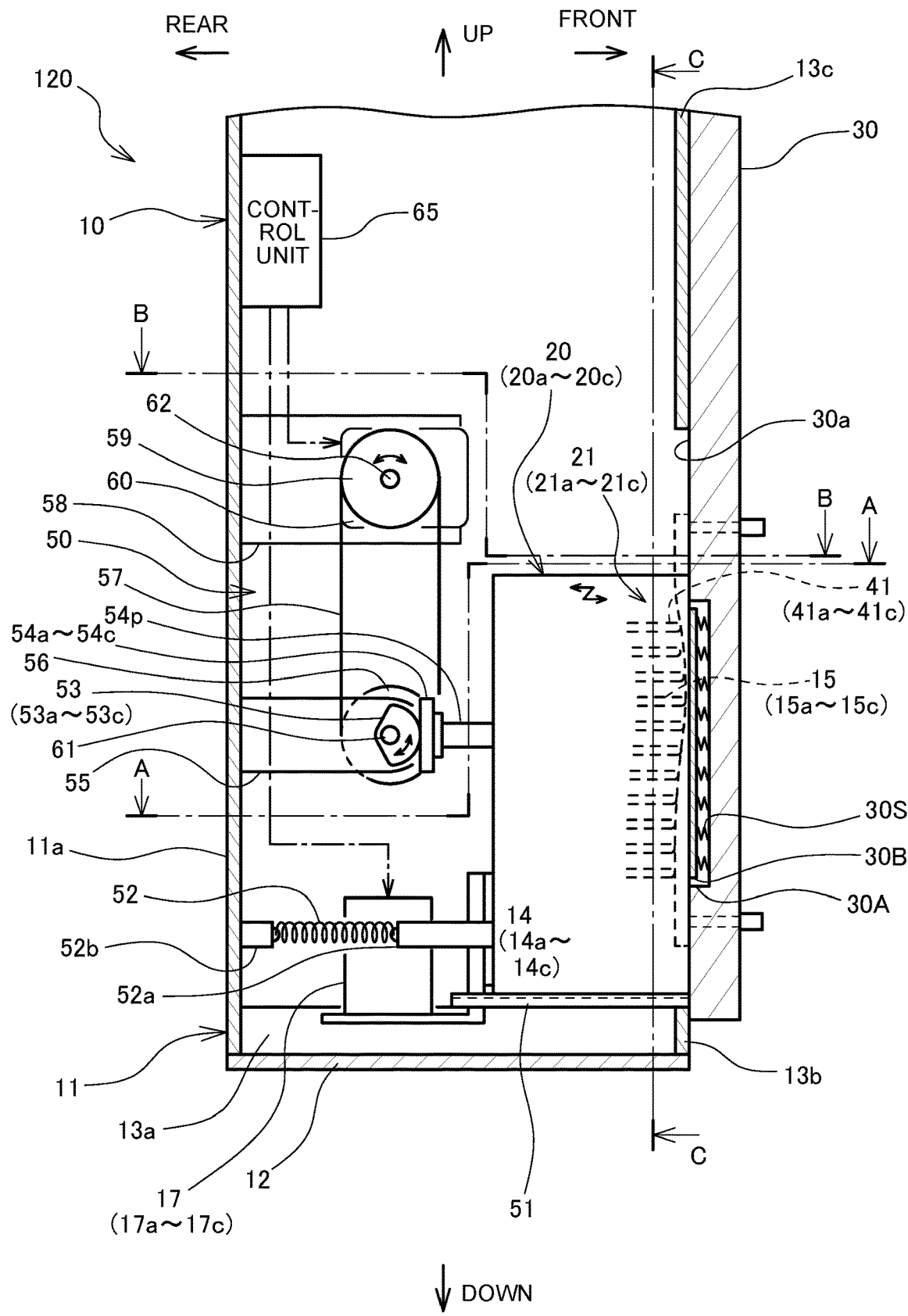
FIG. 27 is an elevational sectional view of a blood purification device according to a further embodiment.
Figure 28:
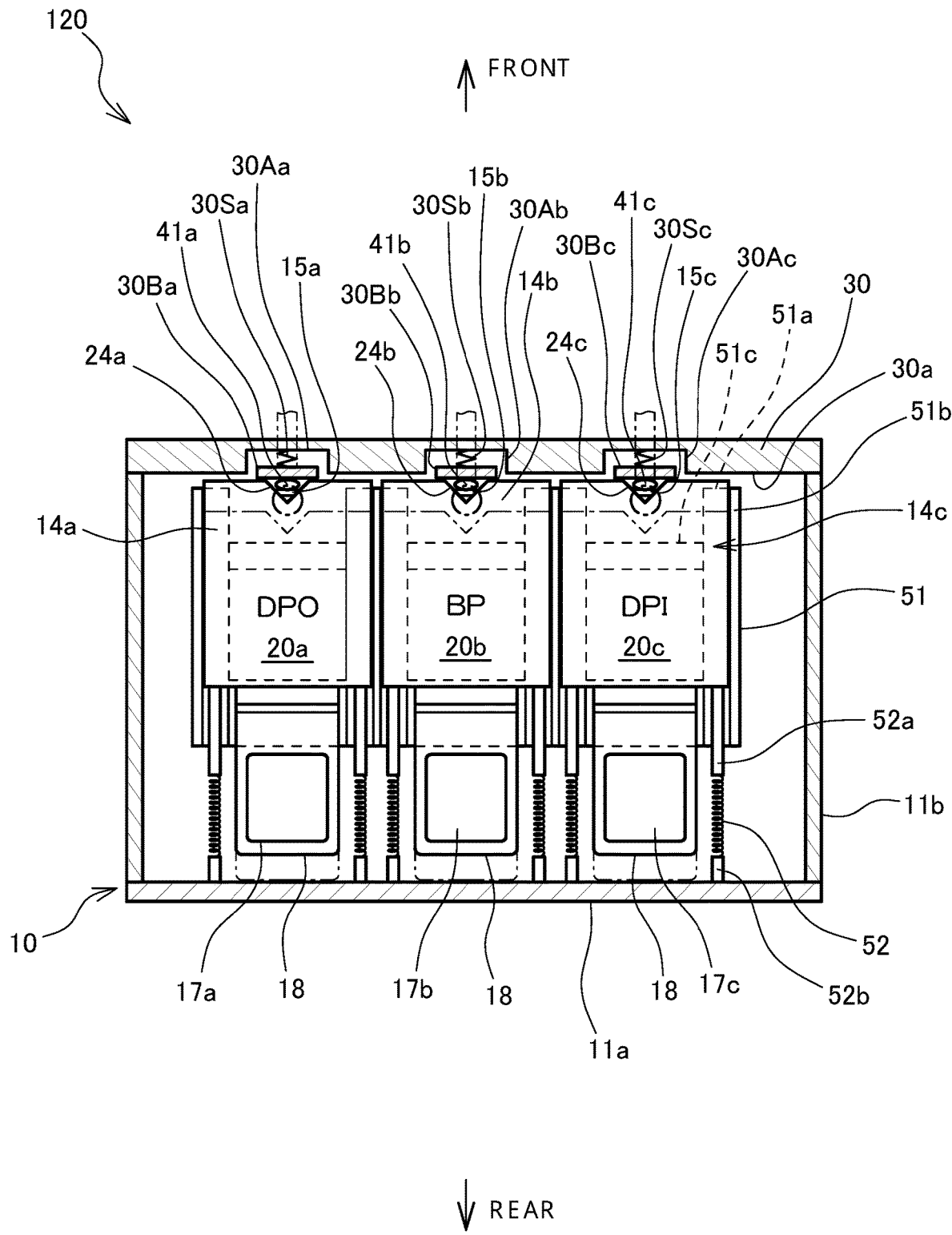
FIG. 28 is a plan sectional view of the blood purification device shown in FIG. 27.

As shown in FIGS. 27 and 28, in the blood purification device 120, recesses 30Aa-30Ac are formed at portions of the cover 30 facing the fingers 15a-15c of the finger driving units 20a-20c, and inside the recesses 30Aa-30Ac, tube support plates 30Ba-30Bc, which are the tube receiving plates, are mounted via adjustment springs 30Sa-30Sc. The pump tube opening/closing mechanism 50 causes the rotary cams 53a-53c to rotate and thereby causes the finger driving units 20a-20c to advance and retract with respect to the tube support plates 30Ba-30Bc, so as to carry out closing and opening of the pump tubes 41a-41c respectively disposed between the fingers 15a-15c of the finger driving units 20a-20c and the tube support plates 30Ba-30Bc. Other structures are identical to those of the blood purification device 100 described above by reference to FIGS. 1-9. So long as the tube support plates 30Ba-30Bc are attached to the cover 30 via the adjustment springs 30Sa-30Sc, it is possible that the configuration includes no recesses 30Aa-30Ac. Further, the portions of the cover 30 abutted by the adjustment springs 30Sa-30Sc may be formed in a protruded shape.

As with the blood purification device 110 described above, the spring constants of the adjustment springs 30Sa-30Sc are greater than the spring constant in the direction in which the pump tubes 41 (41a-41c) are collapsed, are equal to or greater than a spring constant at which the pump tubes 41 (41a-41c) can be completely closed by the reaction force, and are such that, even when the adjustment springs 30Sa-30Sc are compressed, the reaction force does not damage the pump tubes 41 (41a-41c).

Figure 29:
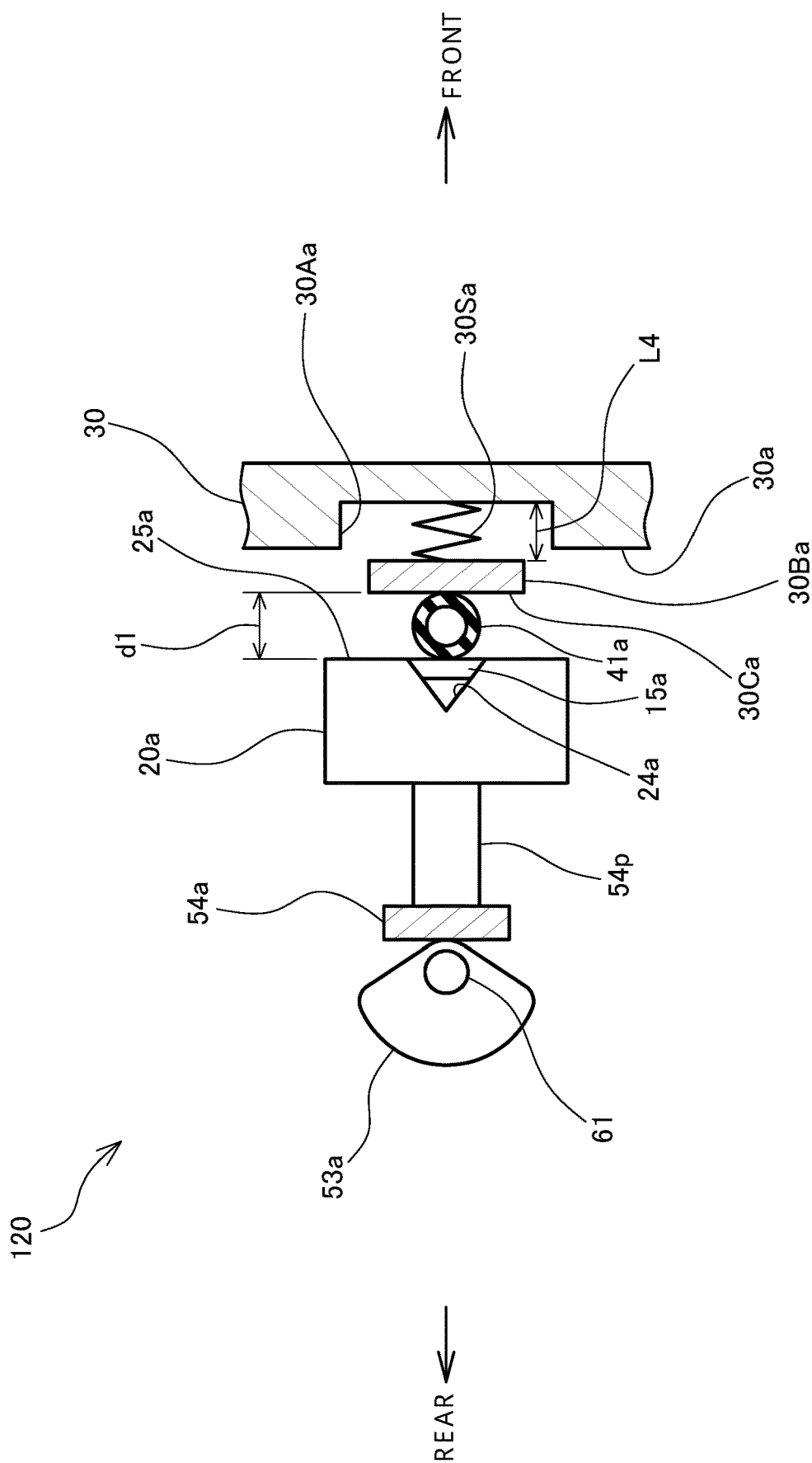
FIG. 29 is a schematic diagram illustrating an initial state in a pump tube closing operation of the blood purification device shown in FIG. 27.
Figure 30:
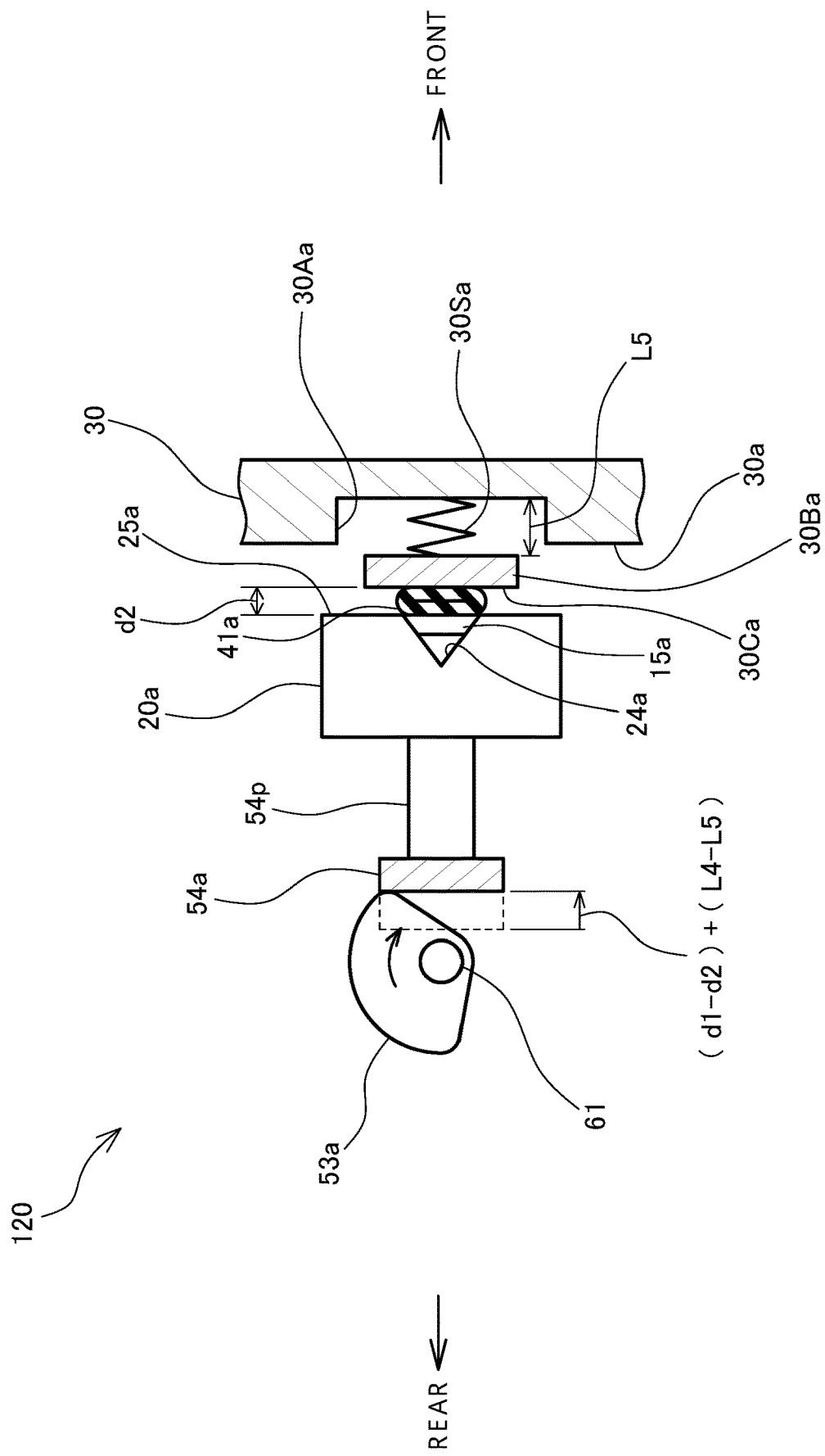
FIG. 30 is a schematic diagram illustrating a state in which the pump tube is collapsed during the pump tube closing operation of the blood purification device shown in FIG. 27.
Figure 31:
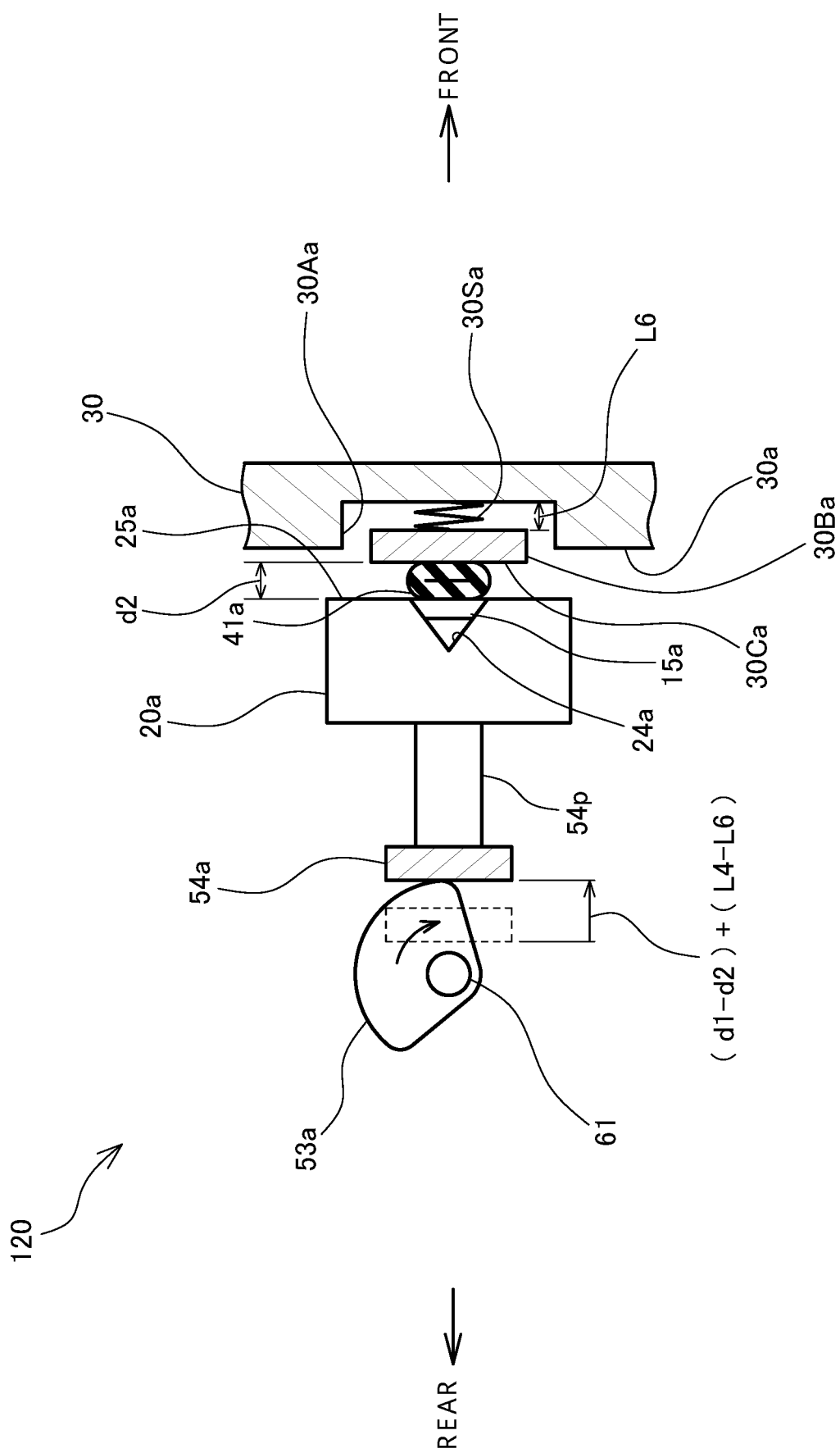
FIG. 31 is a schematic diagram illustrating a state in which an adjustment spring has contracted during the pump tube closing operation of the blood purification device shown in FIG. 27.

A closing operation for closing the pump tube 41a by rotating the rotary cam 53a of the blood purification device 120 and thereby causing the finger driving unit 20a to advance toward the cover 30 will be described by reference to FIGS. 29-31. FIGS. 29-31 are schematic diagrams for explaining the closing operation, and elements shown therein are depicted in a simplified manner. The operation of the finger driving units 20b and 20c is identical to the operation of the finger driving unit 20a.

As shown in FIG. 29, in the initial state, the adjustment spring 30Sa has a reference length L4, and the outer shape of the pump tube 41a has a size d1.

As shown in FIG. 30, when the rotary cam 53a is rotated, the cam follower 54a advances toward the cover 30. As described above, the spring constant of the adjustment spring 30Sa is greater than the spring constant in the direction of squeezing the pump tube 41a. Accordingly, when the cam follower 54a advances toward the cover 30, the pump tube 41a becomes collapsed by being squeezed between the finger 15a and the tube support plate 30Ba. When the rotary cam 53a has rotated and the pump tube 41a is collapsed and placed in the closed state, the pump tube 41a has a thickness d2. At that point, the cam follower 54a has advanced by (d1-d2)+(L4-L5), and the adjustment spring 30Sa has a length L5 that is slightly reduced from the reference length L4.

Next, as shown in FIG. 31, when the rotary cam 53a is rotated further and the cam follower 54a advances further toward the cover 30, the adjustment spring 30Sa starts to contract from the length L4 while the thickness of the pump tube 41a remains d2. At that time, the tube support plate 30Ba enters into the recess 30Aa in the cover 30. Subsequently, when the rotary cam 53a is rotated further and the cam follower 54a advances by (d1-d2)+(L4-L6), the adjustment spring 30Sa contracts to a length L6. At that point, there is a gap between the finger driving unit 20a and the surface 30Ca of the tube support plate 30Ba. The reaction force of the adjustment spring 30Sa at that time is of a magnitude that does not damage the pump tube 41a.

In this way, in the blood purification device 120, after the pump tube 41a is closed, the adjustment spring 30Sa contracts by a length (L5-L6) and thereby absorbs an advancing distance of the cam follower 54a. For this reason, closing and opening of the pump tube 41a can be carried out reliably without adjustment of the advancing distance of the finger driving unit 20a with respect to the cover 30 with high accuracy. In addition, since the reaction force of the adjustment spring 30Sa upon contracting to the length L6 is of a magnitude that does not damage the pump tube 41a, excessive pressing of the pump tube 41a can be avoided, and damages to the pump tube 41a can be suppressed. Although the adjustment spring 30Sa is a coil spring in the blood purification device 120, the adjustment spring 30Sa is not limited thereto, and may alternatively be a leaf spring or may comprise a rubber member.

Figure 32:
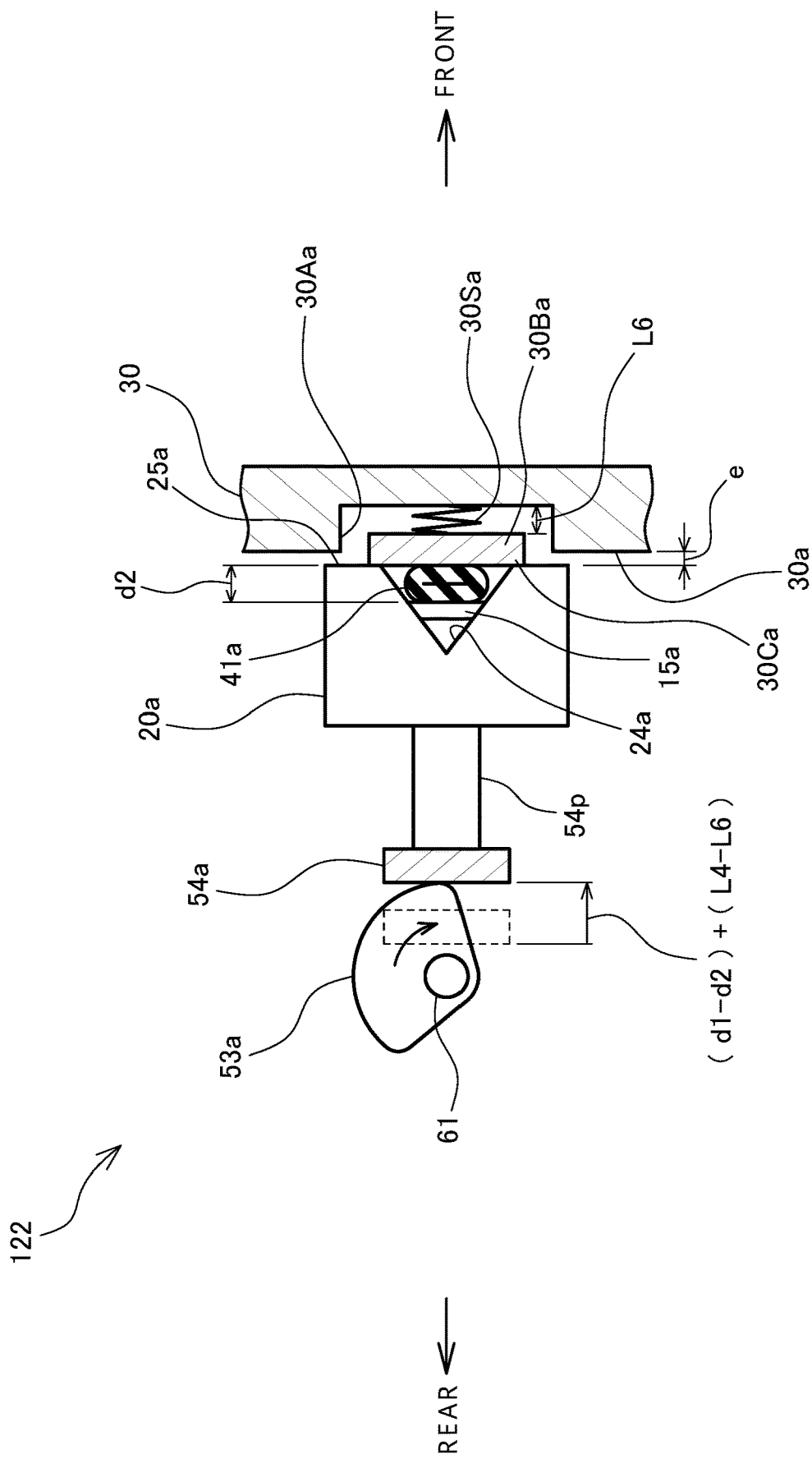
FIG. 32 is a schematic diagram illustrating a state in which an adjustment spring has contracted in a variant of the blood purification device shown in FIG. 27.

Next, a blood purification device 122, which is a variant of the blood purification device 120, will be described by reference to FIG. 32. As shown in FIG. 32, the blood purification device 122 is configured such that, in a state where the finger 15a has moved to the frontmost position, the front end of the finger 15a is located rearward by a distance d2 from the front end 25a of the finger driving unit 20a. The configuration of the finger driving units 20b and 20c is the same as that of the finger driving unit 20a. Other structures are identical to those of the blood purification device 120 described above with reference to FIGS. 27-31.

According to this configuration, as shown in FIG. 32, when the finger 15a closes the pump tube 41a and the thickness of the pump tube 41a becomes d2, the front end 25a of the finger driving unit 20a abuts the surface 30Ca of the tube support plate 30Ba, and the finger 15a does not press the pump tube 41a any further. Here, the spring constant of the adjustment spring 30Sa is adjusted such that, at that point, a gap e is present between the front end 25a of the finger driving unit 20a and the surface 30a of the cover 30. With this arrangement, it is possible to prevent application of an excessive pressing force to the pump tube 41a, and damages to the pump tube 41a can be more effectively suppressed.

Although it has been described that the adjustment springs 54s are respectively provided between the finger driving units 20a-20c and the cam followers 54a-54c in the blood purification devices 110 and 112, and that the adjustment springs 30Sa-30Sc are provided between the finger driving units 20a-20c and the cover 30 in the blood purification devices 120 and 122, embodiments are not limited thereto. For example, an embodiment may be configured such that the adjustment springs 54s are respectively provided between the finger driving units 20a-20c and the cam followers 54a-54c, and in addition, the adjustment springs 30Sa-30Sc are provided between the finger driving units 20a-20c and the cover 30. Further, an embodiment may be configured such that, for a part of the finger driving units 20a-20c, the adjustment springs 54s are respectively disposed between those finger driving units and the cam followers 54a-54c, and for another part of the finger driving units 20a-20c, the adjustment springs 30Sa are disposed between those finger driving units and the cover 30.

Figure 33:
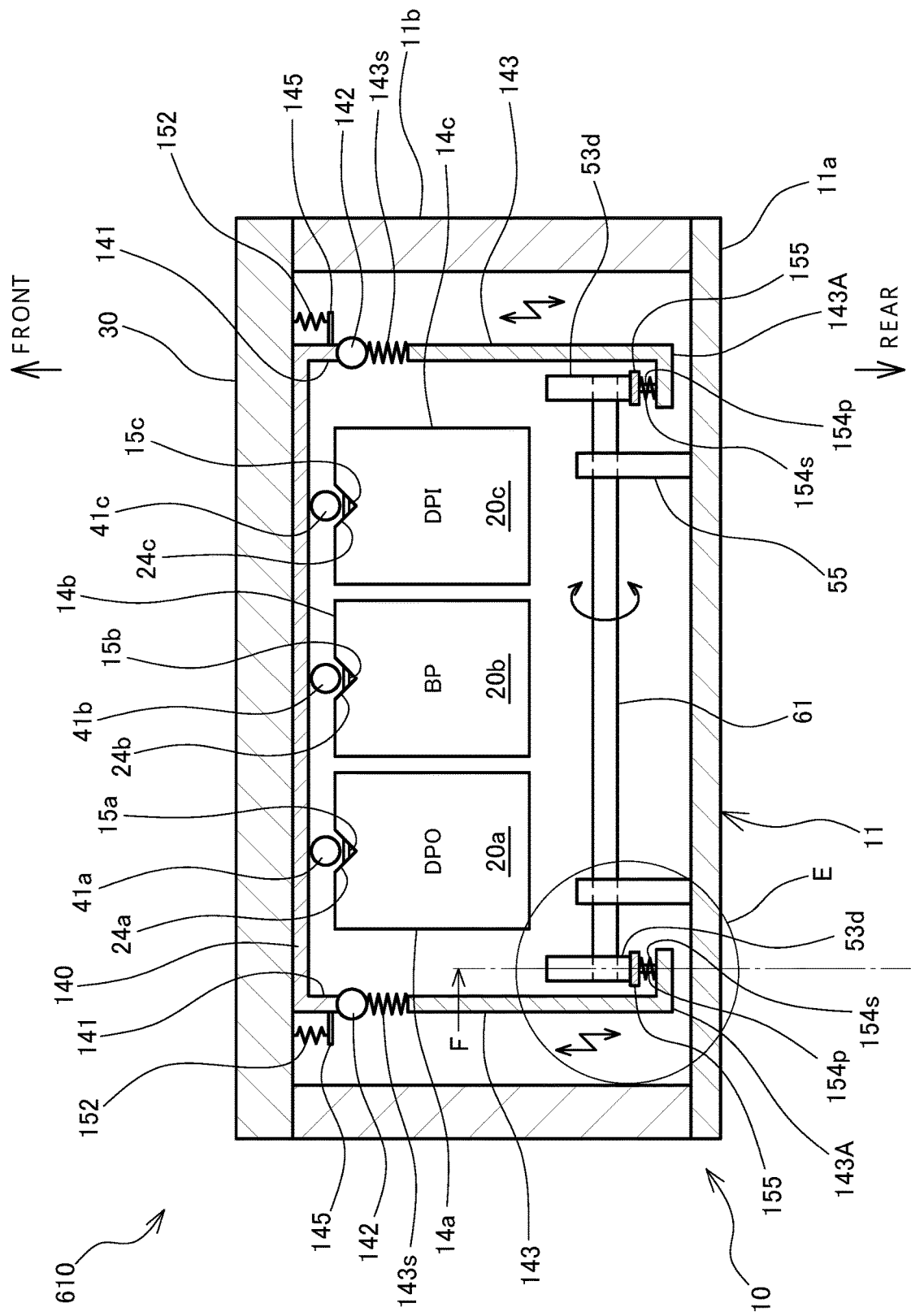
FIG. 33 is a plan sectional view of a blood purification device according to another embodiment.

Next, a blood purification device 610 according to another embodiment will be described by reference to FIGS. 33 and 34. In the blood purification device 610, tips of the cam arms 143 are each formed in an L-shape to thereby provide tip portions 143A that face the rotary cams 53d. Respectively between the tip portions 143A and the rotary cams 53d, cam followers 155 are arranged via adjustment springs 154s, which are elastic members. Further, adjustment springs 143s are provided between the cam arms 143 and the connection mechanisms 142. Other structures are identical to those of the blood purification device 600 described by reference to FIG. 18.

Figure 34:
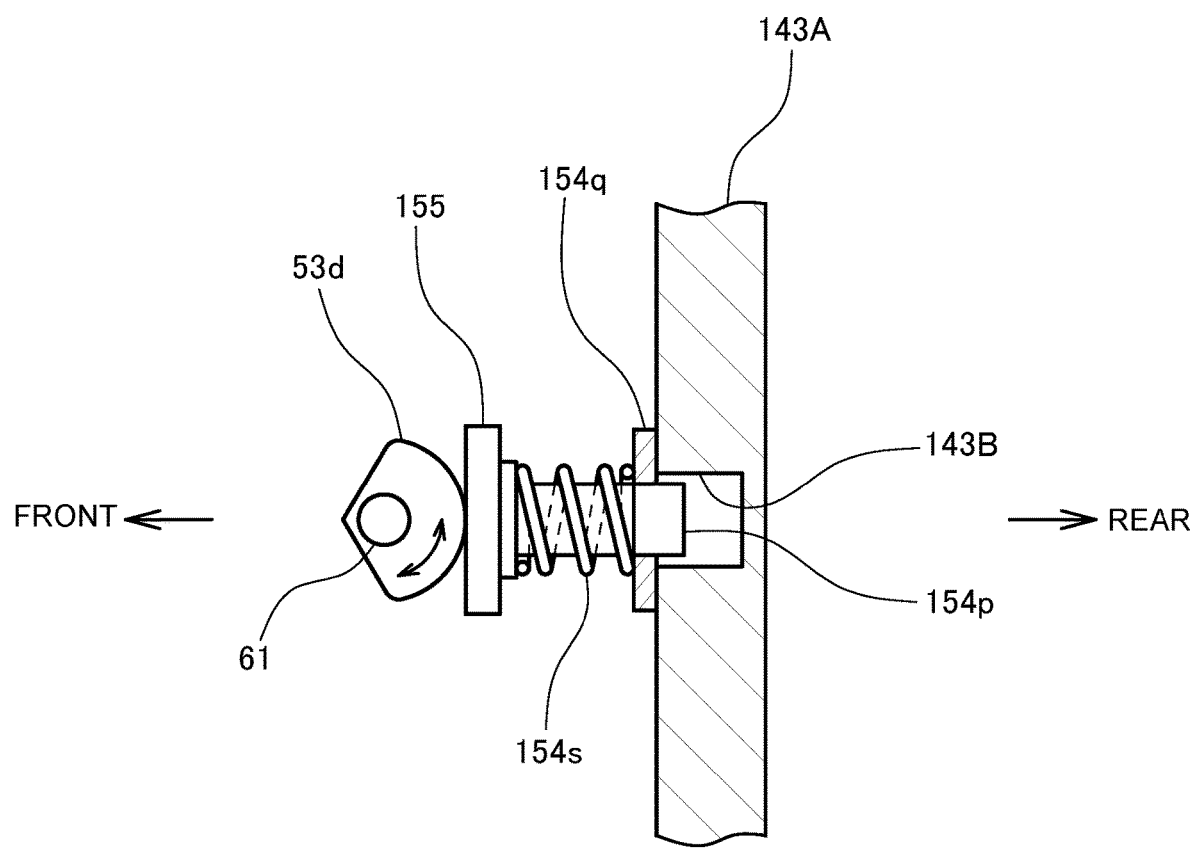
FIG. 34 is an enlarged sectional view of F-F shown in FIG. 33.

As shown in FIG. 34, a post 154p is fixed to a rear part of each cam follower 155, and a recess 143B into which the tip of the post 154p is inserted is formed in the tip portion 143A. Further, a washer 154q having an inner diameter substantially equal to the diameter of the post 154p is fixed to the peripheral edge of the recess 143B in the tip portion 143A. The adjustment spring 154s is mounted to the outer periphery of the post 154p between the washer 154q and the cam follower 155. Although the adjustment spring 154s is a coil spring in the blood purification device 610, the adjustment spring 154s is not limited thereto, and may alternatively be a leaf spring or may comprise a rubber member.

The rotary cam 53a is rotated so as to cause the cam follower 154a to advance toward the tip portion 143A. When the adjustment spring 154s is thereby contracted, the tip of the post 154p advances into the recess 143B in the tip portion 143A.

Similar to the blood purification devices 110 and 120 described above by reference to FIGS. 19-32, in the blood purification device 610, the adjustment springs 154s and 143s contract and thereby absorb an advancing distance of the cam followers 155.

Accordingly, closing and opening of the pump tubes 41a-41c can be carried out reliably without adjustment of the advancing distance of the cam arms 143 with high accuracy, and at the same time, damages to the pump tube 41a-41c can be suppressed.

Although it is explained that, in the blood purification device 610 described above, the adjustment springs 154s and 143s are respectively provided between the tip portions 143A of the cam arms 143 and the rotary cams 53d and between the cam arms 143 and the connection mechanisms 142, embodiments are not limited thereto. An embodiment may be configured such that the adjustment springs are provided at only either one of the above-noted sites. Further, similar to the blood purification device 115 described above by reference to FIG. 26, it may be configured such that the posts 154p are attached to the tip portions 143A without providing the recesses 143B, and through holes to be penetrated by the posts 154p are formed in the cam followers 155.

REFERENCE SIGNS LIST 10 device main body; 11 housing; 11a rear plate; 11b side plate; 12 base; 13a rib; 13b width plate; 13c front plate; 13d ceiling plate; 14, 14a-14c finger casing; 15, 15a-15c finger; 17, 17a-17c drive motor; 56, 59 pulley; 57 belt; 20, 20a-20c finger driving unit; 21, 21a-21c finger support portion; 22 back plate; 23 recess; 24, 24a-24c tube receiving groove; 25a front end; 30 cover; 30a, 32a, 30Ca surface; 30Aa-30Ac, 143B recess; 30Ba-30Bc tube support plate; 30S, 30Sa-30Sc, 54s, 154s adjustment spring; 31 casing; 32 rear plate; 33 weight detection unit; 34, 96a bottom plate; 35 hook; 36 dialyzer; 37 water removal container; 38 dialysate regeneration column; 39 drip chamber; 41, 41a-41c pump tube; 50 pump tube opening/closing mechanism; 51 casing guide; 51a support plate; 51b guide bar; 51c, 54g connecting member; 52, 152 coil spring; 52a, 52b pin; 53, 53a-53d, 75 rotary cam; 54Ha through hole; 54q, 154q washer; 54a-54f, 154, 155 cam follower; 54p, 154p post; 55, 58 bracket; 60 motor; 61, 62, 79 shaft; 63 collar; 65 control unit; 71a-71c projection; 76, 81 first cam surface; 77, 82 second cam surface; 78, 83 third cam surface; 80 plate cam; 84 gear surface; 85 drive gear; 91 blood circuit; 91a blood circuit inlet; 91b blood circuit outlet; 92 dialysate circuit; 93 calibration liquid bag; 94 valve; 95 metal fixture; 96 cassette receiving seat; 96b flange; 100, 110, 112, 115, 120, 122, 200, 300, 400, 500, 600, 610 blood purification device; 130 cassette; 140 tube receiving plate; 141 flange; 142 connection mechanism; 143 cam arm; 143A tip portion; 145 rib; BP blood pump; DPI dialysate inlet pump; DPO dialysate outlet pump.

The invention claimed is:

1. A blood purification device, comprising:
a tube receiving plate that holds an elastic pump tube;
a tube pressing member driving unit which is positioned facing the tube receiving plate across the pump tube, and which causes a tube pressing member to be moved with respect to the tube receiving plate; and
a pump tube opening/closing mechanism that causes the tube pressing member driving unit to advance and retract with respect to the tube receiving plate, and thereby carries out closing and opening of the pump tube which is positioned between the tube pressing member and the tube receiving plate, wherein
the tube receiving plate holds a plurality of pump tubes, each being said pump tube,
the tube pressing member and the tube pressing member driving unit are provided in a plural number,
the pump tube opening/closing mechanism includes:
a plurality of cams that cause the plurality of tube pressing member driving units to advance toward the tube receiving plate, and
a common cam drive unit including a common shaft to which the plurality of cams are attached, and a motor that rotates and drives the shaft, and
the common cam drive unit causes the plurality of tube pressing members to advance or retract with respect to the tube receiving plate at a time so that the plurality of pump tubes are simultaneously closed or opened.

2. The blood purification device according to claim 1, wherein
the pump tube opening/closing mechanism further comprises a plurality of retraction springs that cause the plurality of tube pressing member driving units to retract from the tube receiving plate; and
the pump tube opening/closing mechanism causes the cam driving unit to drive the plurality of cams so that the plurality of tube pressing member driving units are caused to advance and retract with respect to the tube receiving plate, and thereby carries out closing and opening of the plurality of pump tubes, which are positioned between a plurality of tube pressing members, each being said tube pressing member, of the plurality of tube pressing member driving units and the tube receiving plate.

3. The blood purification device according to claim 1, wherein
the plurality of cams have shapes corresponding to combinations of open and closed states of the plurality of pump tubes.

4. The blood purification device according to claim 1, further comprising
a device main body inside of which the plurality of tube pressing member driving units and the pump tube opening/closing mechanism are arranged, wherein
the tube receiving plate is a plate located facing the device main body.

5. The blood purification device according to claim 4, further comprising
a cassette that is detachably mounted to the device main body, wherein
the cassette includes a casing, which contains a dialyzer, a dialysate regeneration column, and a water removal container, and
the tube receiving plate is a plate of the casing that is located facing the device main body.

6. The blood purification device according to claim 1, wherein the tube pressing member is composed of a plurality of fingers.

7. The blood purification device according to claim 1, wherein the plurality of cams cause the plurality of tube pressing member driving units to advance toward the tube receiving plate via a plurality of cam followers, each of which is attached to a corresponding one of the plurality of tube pressing member driving units via an elastic member.

8. The blood purification device according to claim 1, further comprising:
a device main body inside of which the plurality of tube pressing member driving units and the pump tube opening/closing mechanism are arranged; and
a cover attached facing the device main body, wherein the tube receiving plate is attached to the cover via another elastic member.

9. A blood purification device, comprising:
a tube receiving plate that holds an elastic pump tube;
a tube pressing member driving unit which is positioned facing the tube receiving plate across the pump tube, and which causes a tube pressing member to be moved with respect to the tube receiving plate; and
a pump tube opening/closing mechanism that causes the tube receiving plate to advance and retract with respect to the tube pressing member driving unit, and thereby carries out closing and opening of the pump tube which is positioned between the tube pressing member and the tube receiving plate, wherein
the pump tube opening/closing mechanism includes
a plurality of cams that cause the tube receiving plate to advance toward the tube pressing member driving unit, and
a common came drive unit including a common shaft to which the plurality of cams are attached and a motor that rotates and drives the common shaft, and
a retraction spring that causes the tube receiving plate to retract from the tube pressing member driving unit,
the tube receiving plate holds a plurality of pump tubes, each being said pump tube,
the tube pressing member and the tube pressing member driving unit are provided in a plural number, and
the cam drive unit of the pump tube opening/closing mechanism causes the tube receiving plate to advance and retract with respect to the plurality of tube pressing member driving units in such a manner that the tube receiving plate simultaneously closes or opens the plurality of pump tubes, which are positioned between the plurality of tube pressing members of the plurality of tube pressing member driving units and the tube receiving plate.

10. The blood purification device according to claim 9, wherein the pump tube opening/closing mechanism includes:
a plurality of cam arms connected to the tube receiving plate; and
a plurality of cam followers, each of which is attached to a corresponding one of the plurality of cam arms via an elastic member, wherein
the plurality of cams cause the tube receiving plate connected to the plurality of cam arms via the plurality of cam followers to advance toward the tube pressing member driving unit.

11. The blood purification device according to claim 10, wherein the tube receiving plate and the plurality of cam arms are connected via another elastic member.

12. The blood purification device according to claim 9, wherein the tube pressing member is composed of a plurality of fingers.

* * * * *